US012642853B2

(12) United States Patent
Kang

(10) Patent No.: US 12,642,853 B2
(45) Date of Patent: Jun. 2, 2026

(54) USE OF COMPOSITION IN TREATING ATHEROSCLEROSIS

(71) Applicant: INNOCORUN Co., Ltd., Chengdu (CN)

(72) Inventor: Yujian James Kang, Chengdu (CN)

(73) Assignee: INNOCORUN CO., LTD., Chengdu (CN)

( * ) Notice: Subject to any disclaimer, the term of this patent is extended or adjusted under 35 U.S.C. 154(b) by 805 days.

(21) Appl. No.: 17/904,687

(22) PCT Filed: Feb. 7, 2021

(86) PCT No.: PCT/CN2021/075877
§ 371 (c)(1),
(2) Date: Aug. 19, 2022

(87) PCT Pub. No.: WO2021/164600
PCT Pub. Date: Aug. 26, 2021

(65) Prior Publication Data
US 2023/0104799 A1     Apr. 6, 2023

(30) Foreign Application Priority Data

| Feb. 20, 2020 | (CN) | .......................... 202010104393.6 |
| Sep. 22, 2020 | (CN) | .......................... 202011004941.4 |

(51) Int. Cl.

| A61K 41/00 | (2020.01) |
| A61K 9/00 | (2006.01) |
| A61K 33/34 | (2006.01) |
| A61K 47/69 | (2017.01) |
| A61P 9/10 | (2006.01) |

(52) U.S. Cl.
CPC ........ *A61K 41/0028* (2013.01); *A61K 9/0019* (2013.01); *A61K 33/34* (2013.01); *A61K 47/6925* (2017.08); *A61P 9/10* (2018.01)

(58) Field of Classification Search
CPC .. A61K 41/0028; A61K 9/0019; A61K 33/34; A61K 47/6925; A61P 9/10
See application file for complete search history.

(56) References Cited

U.S. PATENT DOCUMENTS

| 2013/0123781 A1* | 5/2013 | Grubbs ................... A61P 35/00 |
| | | 606/45 |
| 2018/0099008 A1* | 4/2018 | Kang ................... A61K 9/0019 |

FOREIGN PATENT DOCUMENTS

| CN | 101926821 A | 12/2010 |
| CN | 102302507 A | 1/2012 |
| CN | 103917637 A | 7/2014 |
| CN | 110201194 A | 9/2019 |

(Continued)

OTHER PUBLICATIONS

CN101926821A English translation (Year: 2010).*

(Continued)

*Primary Examiner* — Sahana S Kaup
*Assistant Examiner* — Joshua A Atkinson
(74) *Attorney, Agent, or Firm* — Knobbe, Martens, Olson & Bear, LLP

(57) ABSTRACT

Disclosed in the present application is a use of a composition in treating atherosclerosis. Specifically, the present application relates to a use of a composition comprising microbubbles and copper ions in treating atherosclerosis.

17 Claims, 15 Drawing Sheets

(56) References Cited

FOREIGN PATENT DOCUMENTS

| CN | 111297895 | A | 6/2020 |
| CN | 111991420 | A | 11/2020 |
| WO | 2011/109334 | A2 | 9/2011 |

OTHER PUBLICATIONS

Lamb et al, "Dietary copper supplementation reduces atherosclerosis in the cholesterol-fed rabbit", Atherosclerosis, 1999, vol. 146, issue 1, pp. 33-43 (Year: 1999).*
Chemistry Job Insight, "Understanding Standard Conditions: IUPAC, STC, NTP, and SATP", 2025. Retrieved from https://www. chemistryjobinsight.com/2025/03/understanding-standard-conditions-iupac-stc-ntp-satp.html (Year: 2025).*
International Search Report issued for International Patent Application No. PCT/CN2021/075877, dated Apr. 26, 2021 In 5 pages.
Pan et al., "Effect of Dietary Zinc and Copper on Rat Serum Lipids"; Studies of Trace Elements and Health (1995), English abstract only.
Gao et al., "Copper sulfide nanoparticles as a photothermal switch for TRPV1 signaling to attenuate atherosclerosis"; Nature Communications, 9:231 (2018).

* cited by examiner

A                    B                    C

Normal group     Pre-intervention group     Non-intervention group     Microbubble group     Cu-microbubble group Pre-intervention group     Non-intervention group     Microbubble group     Cu-microbubble group Pre-intervention group    Non-intervention group    Microbubble group    Cu-microbubble group Pre-intervention group    Non-intervention group    Microbubble group    Cu-microbubble group Pre-intervention group    Non-intervention group    Microbubble group    Cu-microbubble group Pre-intervention group     Non-intervention group     Microbubble group     Cu-microbubble group

USE OF COMPOSITION IN TREATING ATHEROSCLEROSIS

CROSS-REFERENCE TO RELATED APPLICATIONS

The present application is the U.S. National Phase under 35. U.S.C. § 371 of International Application PCT/CN2021/075877, filed Feb. 7, 2021, which claims priority to two Chinese Patent Applications Nos. 202011004941.4 filed on Sep. 22, 2020 and 202010104393.6 filed on Feb. 20, 2020, and the entire contents of which are incorporated herein by reference in their entireties.

TECHNICAL FIELD

The present invention relates to the treatment of atherosclerosis, and in particular to the therapeutic use of therapeutic agents carried by microbubbles for the treatment of atherosclerosis.

BACKGROUND ART

Healthy arteries are elastic, but over time the walls of the arteries will harden, a condition commonly known as arteriosclerosis. The lesion of the affected artery starts from the intima with local lipid accumulation, fibrous tissue proliferation and calcinosis, forming plaques. It is called atherosclerosis because of the yellow atheromatous appearance of lipids that accumulate in the intima of the arteries. It is the most common disease in cardiovascular and cerebrovascular system diseases, mainly affecting the large and medium arteries in the body, such as coronary artery, carotid artery, cerebral artery, and renal artery.

Atherosclerosis is a slowly progressive disease that may begin in childhood with no obvious symptoms in the early stage and then develop into dizziness and chest tightness. Every year, about 20 million people worldwide die from atherosclerotic diseases. At present, the main methods of treating atherosclerosis include drug therapy, surgical treatment and the like. Drug therapy mainly includes: administration of blood lipid-lowering drugs, antiplatelet drugs, vasodilator drugs, thrombolytic and anticoagulant drugs and the like; surgical treatment is mainly aimed at recanalization, reconstruction or bypass grafting of stenotic or occluded arteries, and it is also feasible to implement intravascular stent placement and other interventional treatments.

Wen Gao et al. disclosed the use of CuS as a photothermal material to open the TRPV1 channel supplemented by laser irradiation to reduce atherosclerosis in "Copper sulfide nanoparticles as a photothermal switch for TRPV1 signaling to attenuate atherosclerosis" (Nature Communications, (2018) 9:231).

Chinese Patent Application Publication No. CN103917637A discloses a "targeting microbubble" comprising a fluid-containing core, an anchoring moiety and a targeting moiety, the microbubble can be targeted to a calcium-containing tissue or lesion such as concretion, atherosclerotic plaque, calcified tissue or plaque by a chemical group (i.e., a phosphonic acid group) having affinity for calcium ions, and the microbubble is ruptured through cavitation action (e.g., using electromagnetic energy or ultrasonic energy) to release energy sufficient to cause destruction (e.g., dissolution or fragmentation) of the target tissue or lesion (e.g., calculus, plaque and the like). However, no specific method or effect of treatment for atherosclerotic plaque is disclosed in this patent application. More-over, this method may cause plaque fragmentation, and the fragmented parts may lead to serious consequences such as embolism along with blood circulation.

Therefore, there remains a need for effective and safe medicaments and methods for the treatment of atherosclerosis.

SUMMARY OF THE INVENTION

In view of this, it is a main object of the present invention to provide a pharmaceutical use of a medicament that is effective in treating atherosclerosis and does not cause plaque fragmentation and shedding.

To this end, the present invention provides a use of a composition comprising microbubbles and copper ions in the preparation of a medicament for the treatment of atherosclerosis.

The composition of the present invention can be used for the treatment of atherosclerosis present in arteries at any site, including in particular the treatment of atherosclerosis in the aorta (e.g., thoracic and abdominal aortas) and coronary arteries. The composition of the present invention also has a therapeutic effect on related diseases caused by atherosclerosis (such as coronary heart disease caused by coronary atherosclerosis).

The composition comprises: a solution comprising microbubbles having a concentration greater than $1 \times 10^6$/mL and a particle size less than 10 μm and an effective therapeutic amount of copper ions, wherein the microbubble has a core-envelope structure, the core of the microbubble contains a fluid, and the envelope of the microbubble is composed of a pharmaceutically acceptable film-forming material.

The fluid contained in the core of the microbubble is gaseous in the environment within the patient's body. The fluid is inert and has a boiling point under standard conditions of lower than 35° C., preferably a boiling point lower than 30° C. When the fluid is released in the body, it can be easily excreted out of the body in the form of a gas with substantially no side effect. Examples of such fluids include air, carbon dioxide, C1-6 fluoroalkanes (such as perfluoropropane, pentafluoropentane and the like). Particularly preferably the fluid is perfluoropropane.

The pharmaceutically acceptable film-forming material may be, but is not limited to, a material such as albumin or phospholipid. According to a specific embodiment, human serum albumin is more preferred. The microbubbles of the present invention may be those conventionally used as acoustic contrast agents (e.g., but not limited to, AlBUNEX®, DEFINITY®, OPTISON® and the like). Furthermore, microbubbles other than acoustic contrast agents are also possible. For example, the microbubbles of the present invention may be microbubbles that remain stable in the circulatory system and are observable by contrast ultrasound, but tend to rupture under the vibration of high-energy ultrasound. For example, the envelope of the microbubble of the present invention may be composed of human serum albumin.

The copper ion and the pharmaceutically acceptable film-forming material form a complex, preferably a chelate.

According to one embodiment, the surface of the envelope of the microbubble may further have a targeting moiety that facilitates enrichment of the microbubbles to atherosclerotic plaques. The targeting moiety may be a chemical group having a substituent that can chelate calcium. The substituent may be an amino group, a carboxyl group, a phosphoryl group, and a sulfydryl group and the like. In particular, the targeting moiety may have a bisphosphonate group belonging to the family of bone targeting agents.

According to one embodiment, the concentration of the microbubbles is $0.5 \times 10^7$ to $1.5 \times 10^7$/mL, preferably $1.0 \times 10^7$ to $1.3 \times 10^7$/mL.

The microbubbles may have an average diameter of 1 to 5 μm, preferably 1 to 2 μm.

The effective therapeutic amount of $Cu^{2+}$ may be $Cu^{2+}$ having a concentration of 35 to 105 mg/mL in the composition, preferably $Cu^{2+}$ having a concentration of 45 to 85 mg/mL.

The composition may further comprise a pharmaceutically acceptable carrier. Specifically, the carrier may be a dextrose solution, physiological saline or deionized water.

Accord to a specific embodiment, the medicament is an injection. More specifically, the medicament is an injection or a powder injection. For example, the medicament may be in the form of a solution of the composition, or the composition in the form of a solution may be lyophilized to obtain the medicament in the dosage form of a powder injection.

According to a specific embodiment, cavitation of the microbubbles may be caused upon application of external energy to the medicament.

In particular, the energy is ultrasonic energy or electromagnetic energy.

In embodiments of the present invention, the treatment of atherosclerosis is inhibiting atherosclerotic plaque size growth and/or reducing atherosclerotic plaque size.

The atherosclerotic plaque may be an atherosclerotic plaque at any stage.

It is an object of the second aspect of the present invention to provide a composition as defined above for the treatment of atherosclerosis.

It is an object of the third aspect of the present invention to provide a method of treating atherosclerosis, comprising the following steps: injecting a composition as defined above into a blood vessel of a subject, and applying external energy to a vascular site to be treated.

According to a specific embodiment, the applied external energy can cause cavitation of the microbubbles in the composition.

More specifically, the applied external energy is ultrasonic energy or electromagnetic energy.

As can be seen from the examples which will be described in detail below, some atherosclerotic plaques occurring in the arteries of the tested animals are either in the fatty streak stage (white fatty streaks on the surface of arterial intima), and some are in the fibrous plaque stage (smooth muscle cell hyperplasia, collagen hyperplasia, and macrophage infiltration are observed in plaques according to pathological sections), and the composition can be effective to both stages. Therefore, the composition can be used for the treatment of atherosclerosis at any stage, can significantly reduce or inhibit the development of plaques, can even reduce the area and volume of the plaques and reduce the content of fatty (especially total cholesterol and sphingomyelin) in the plaques compared with prior treatment. Since the composition acts through copper ions, it has no effect on the stability of the plaque, and does not cause the peeling of the plaque, so it can be used safely.

Figure 2:
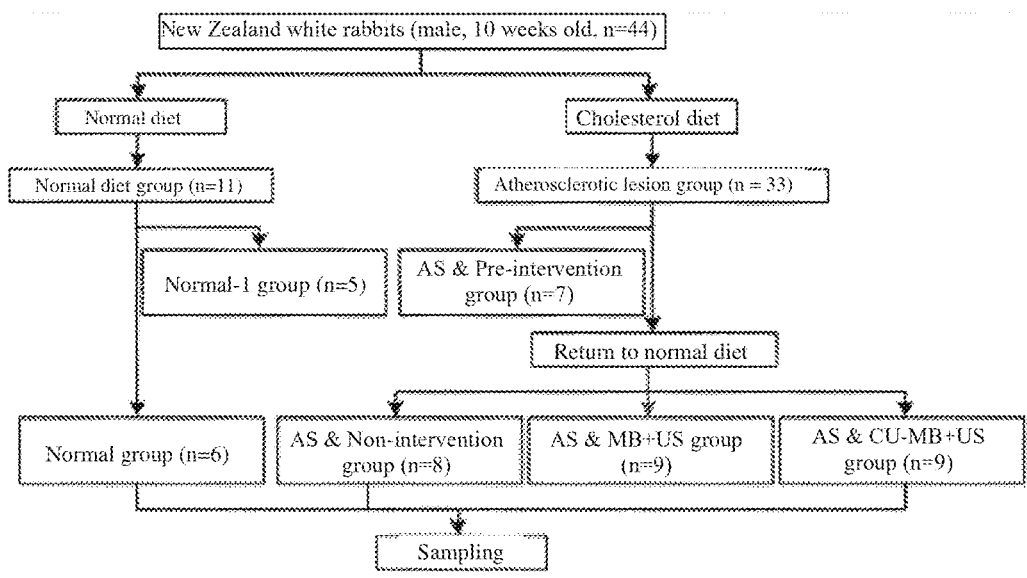
Figure 3:
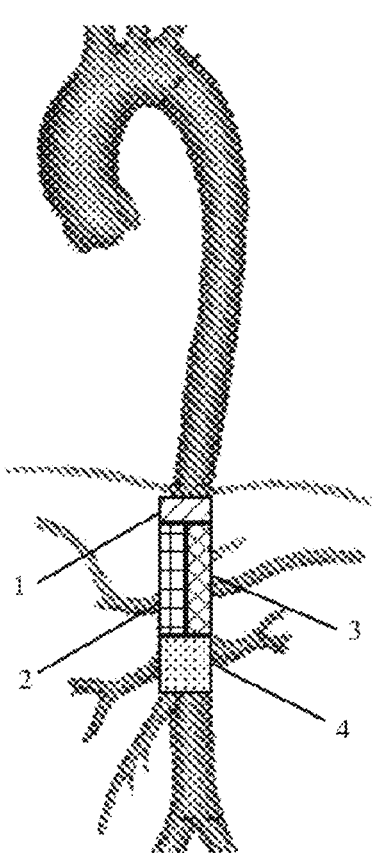
Figure 4:
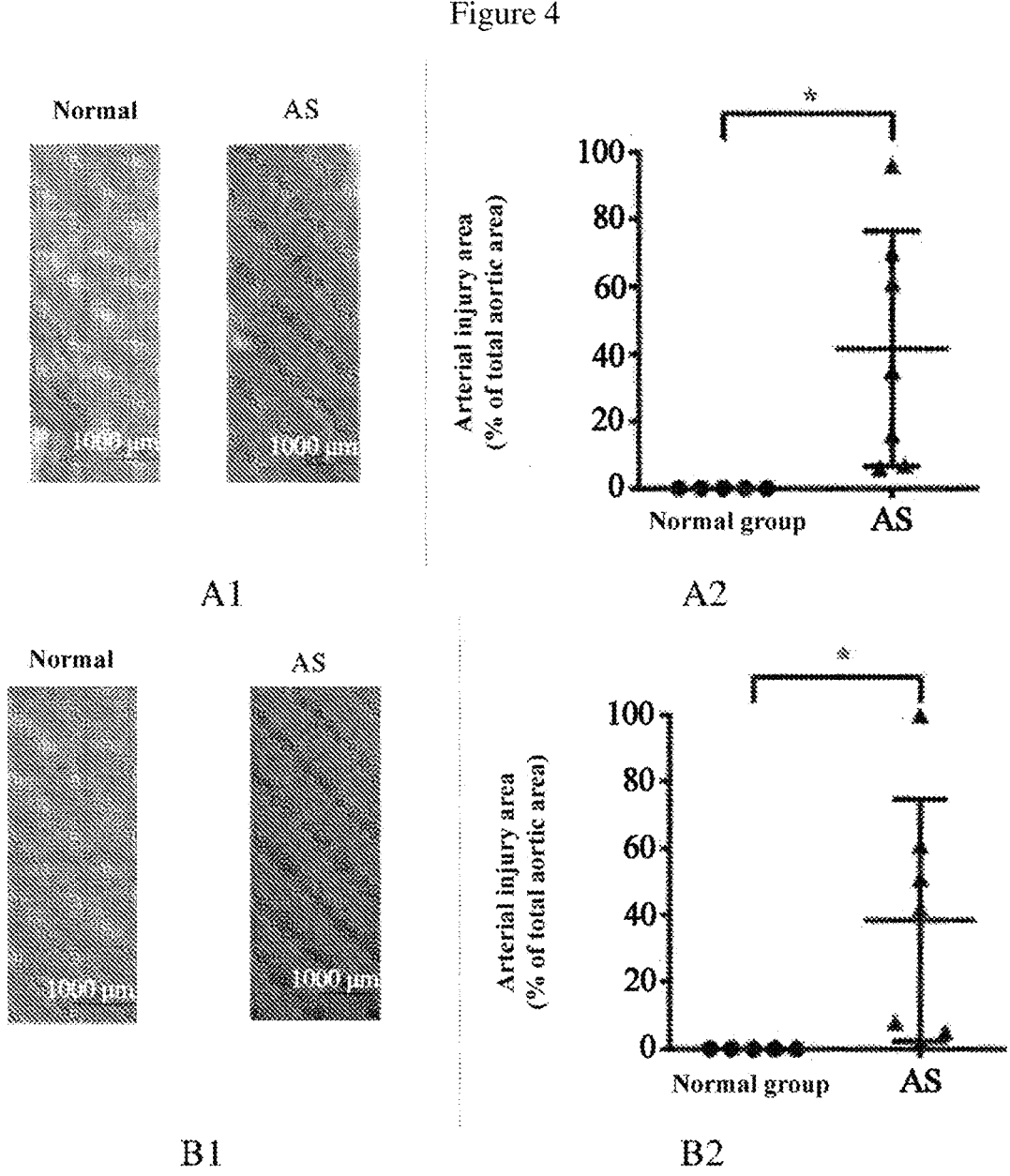
Figure 5:
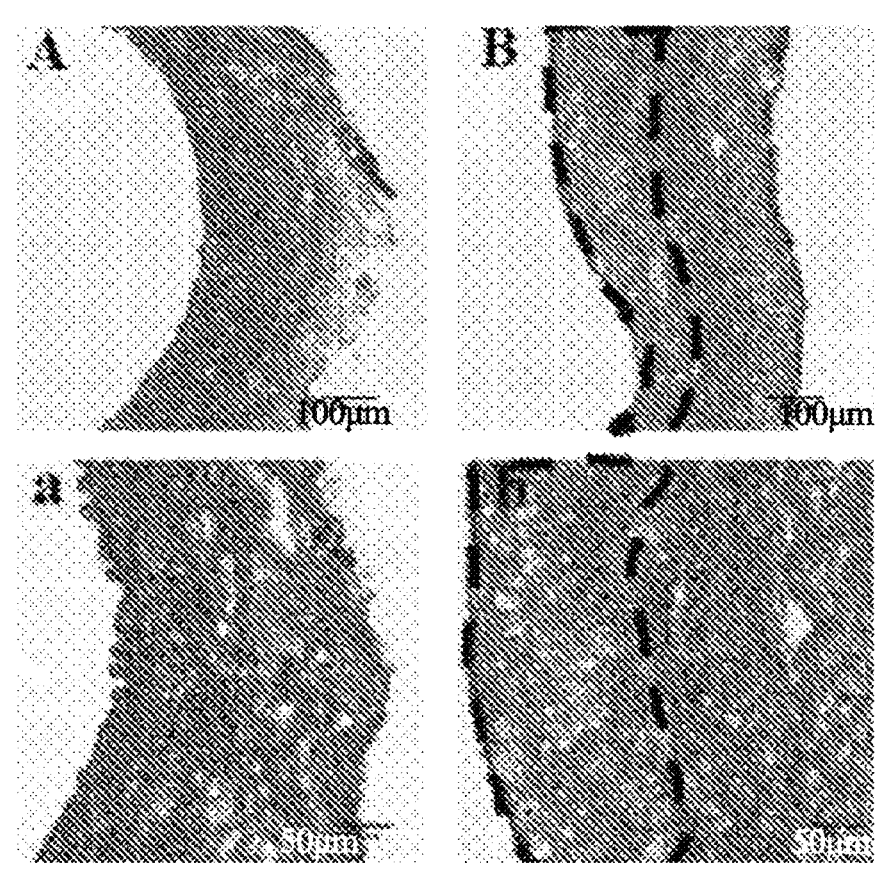

4 batches of compositions prepared by the preparation method of samples Nos. 3, 10, 11 and 12 in the Preparation Examples;

FIG. 2 shows the establishment and grouping flow chart of the animal model used in the Examples;

FIG. 3 is a schematic diagram of tissue allocation for different tests on the aorta in Example 4;

FIG. 4 shows the results of Oil Red O stained aorta after being fed for 12 weeks in the normal diet group and the high-cholesterol diet group in the animal model experiment established in Example 3, wherein A1 is a photo of the abdominal aorta after staining, scale=1000 μm, A2 is the statistical result of the percentage of the area of stained plaques to the vascular tiled area, and two-sided test is performed for t-test, $*p<0.05$; B1 is the photograph of the thoracic aorta after staining, scale=1000 μm, and B2 is the statistical result of the percentage of the area of stained plaque to the vascular tiled area, and two-sided test is performed for t-test, $*p<0.05$;

FIG. 5 is a light microscope photograph of the transverse section of abdominal aorta tissue stained with hematoxylin and eosin of the normal diet group and the high-cholesterol diet group after being fed for 12 weeks in the animal model experiment established in Example 3, wherein A and a are the normal diet group, and it can be seen that intima is smooth and no plaques are seen; B and b are the high-cholesterol diet group, and it can be seen that plaques are formed under the intima. In the figure, the scale of A and B=100 μm, and the scale of a and b=50 μm.

Figure 6:
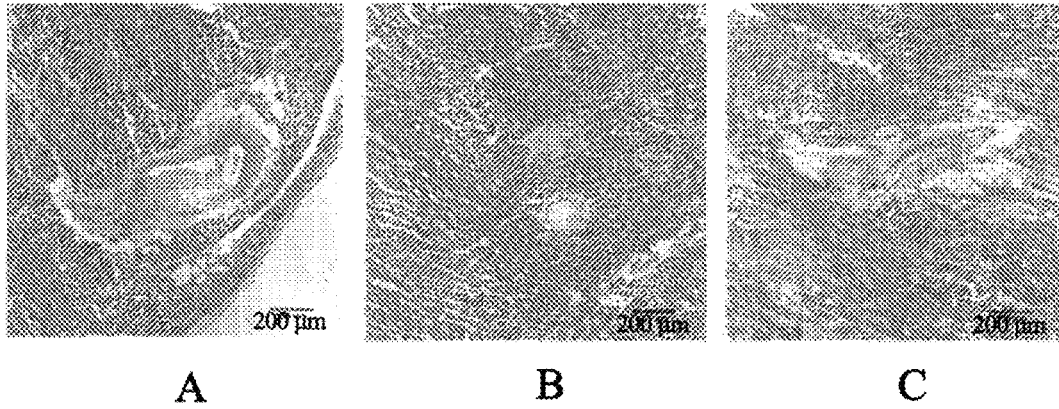
Figure 7:
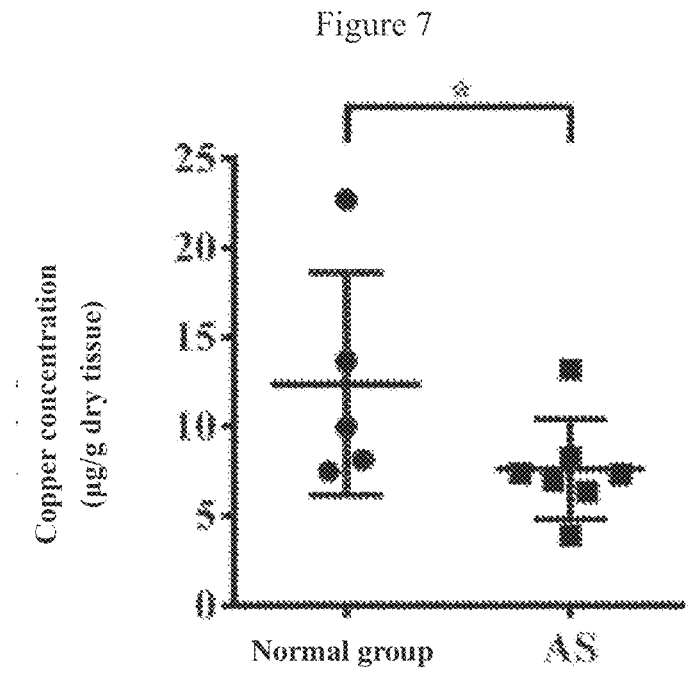
Figure 8:
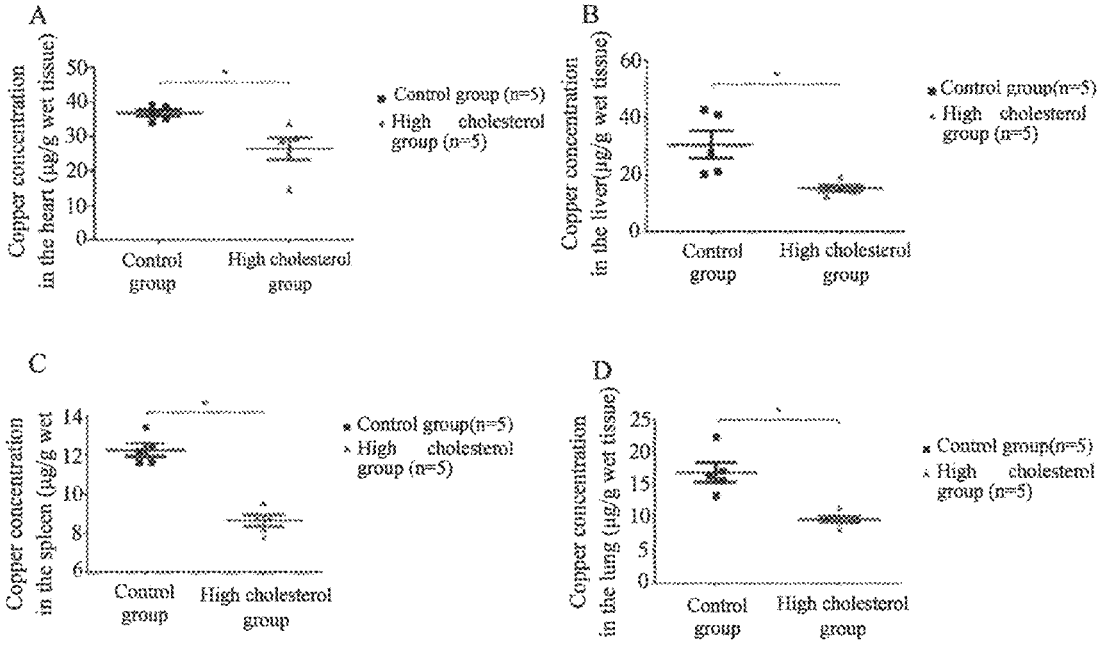
Figure 9:
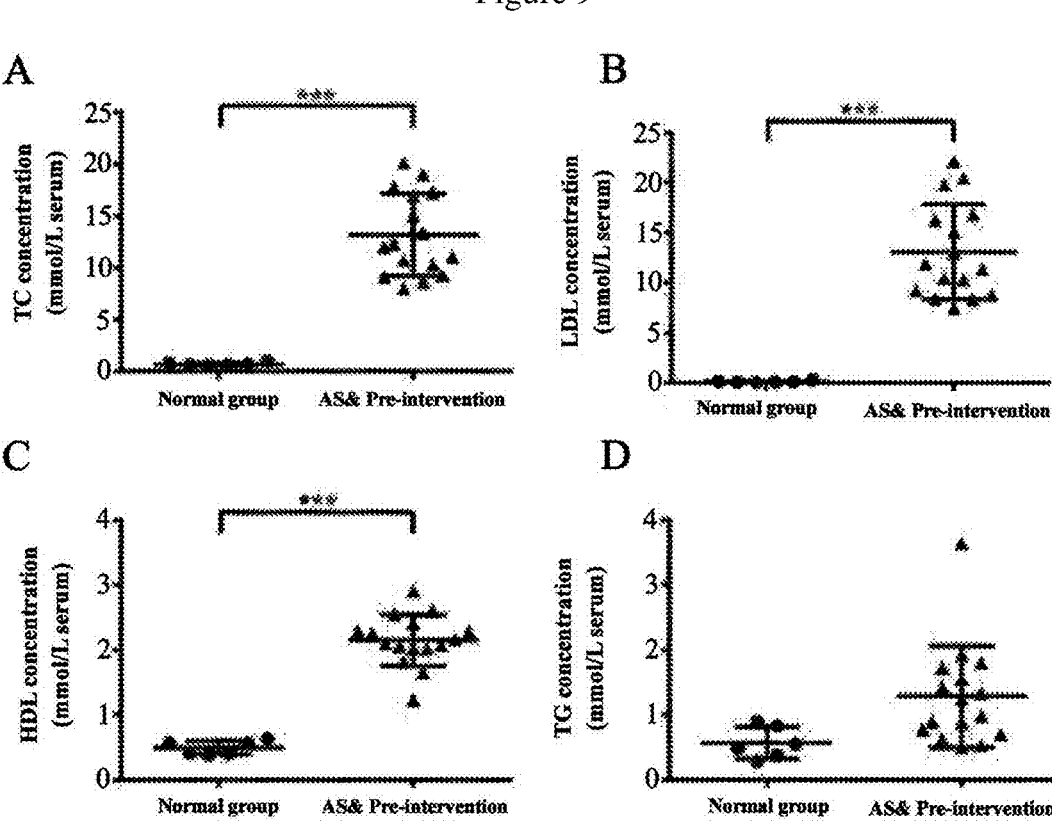
Figure 10:
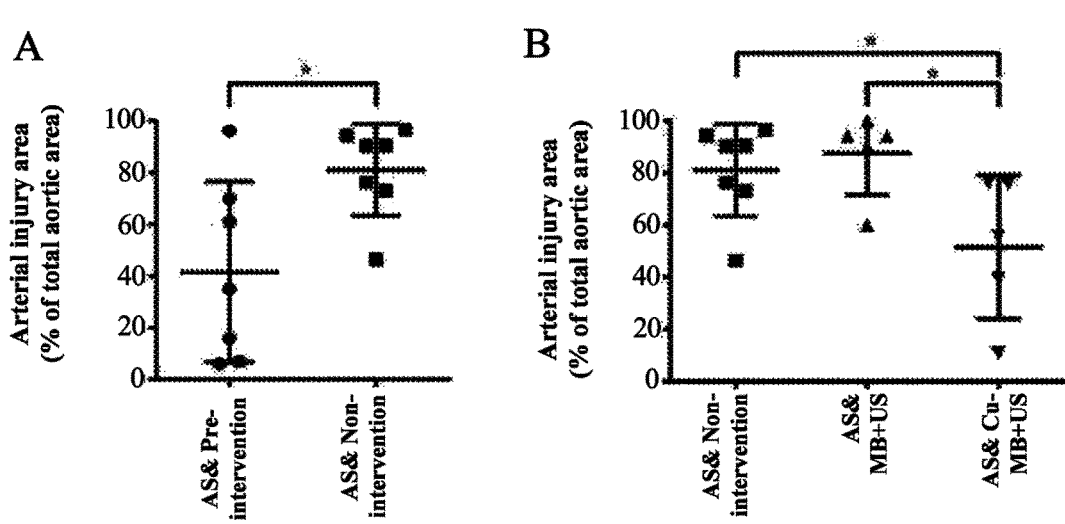
Figure 11:
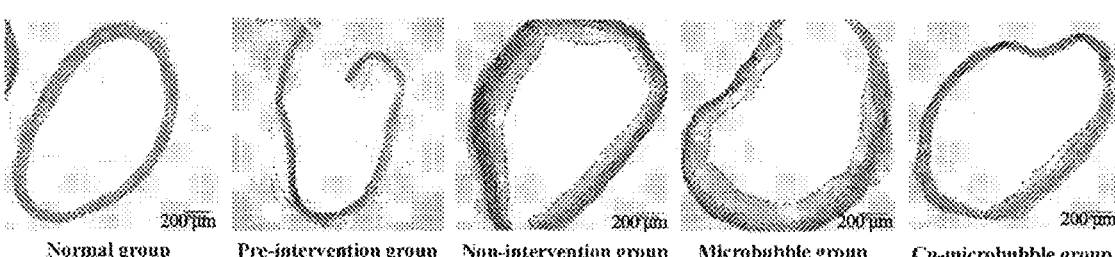
Figure 12:
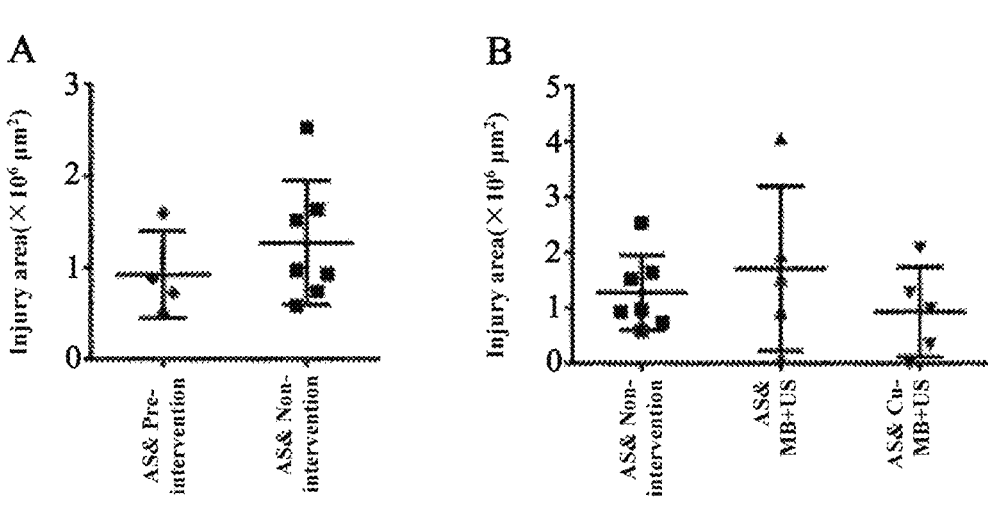
Figure 13:
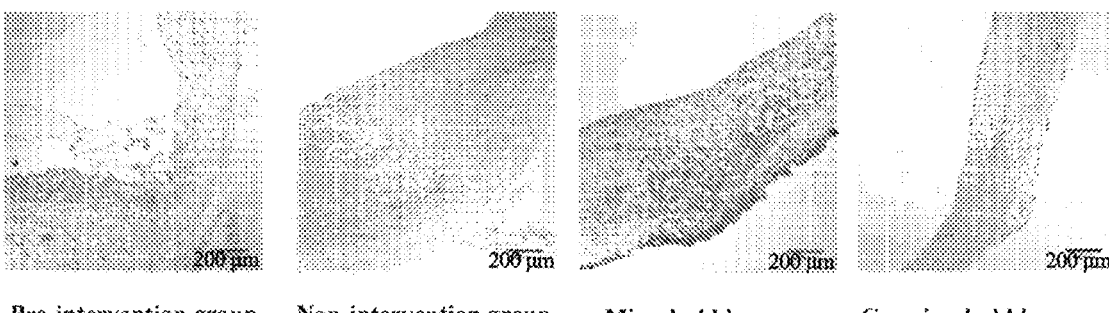
Figure 14:
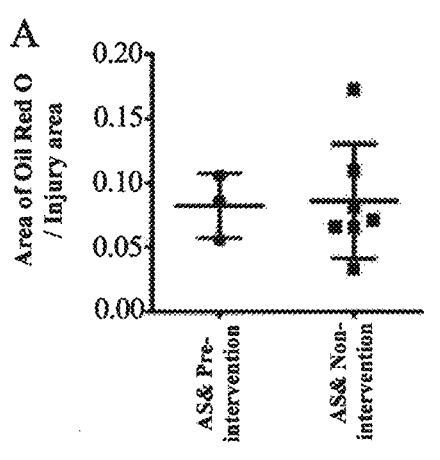
Figure 14:
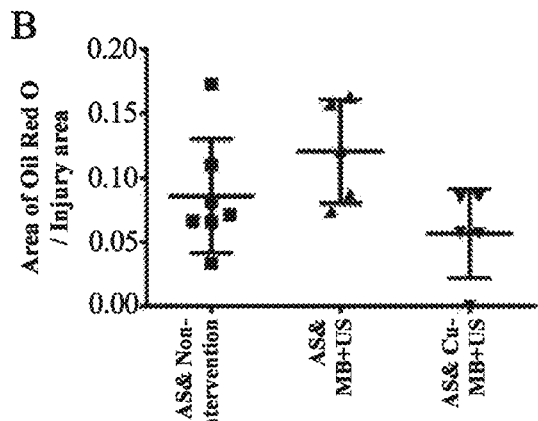
Figure 15:
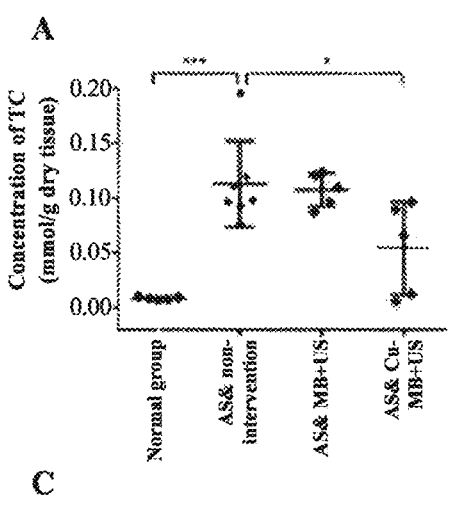
Figure 15:
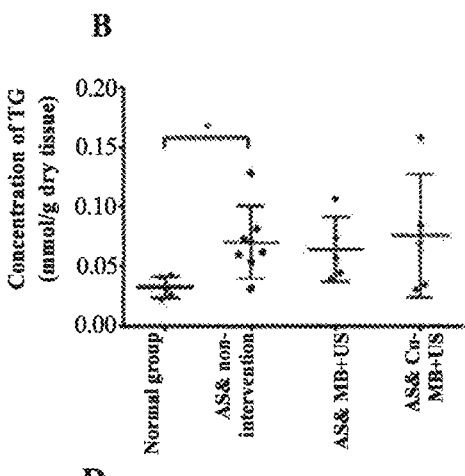
Figure 15:
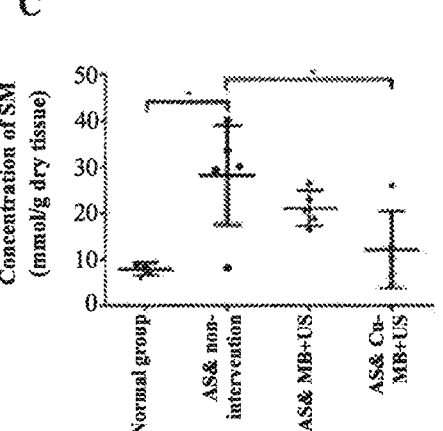
Figure 15:
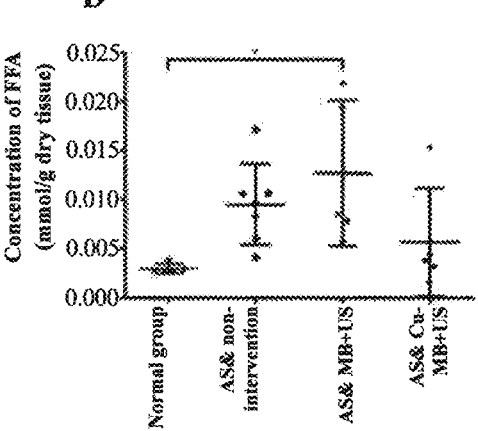
Figure 16:
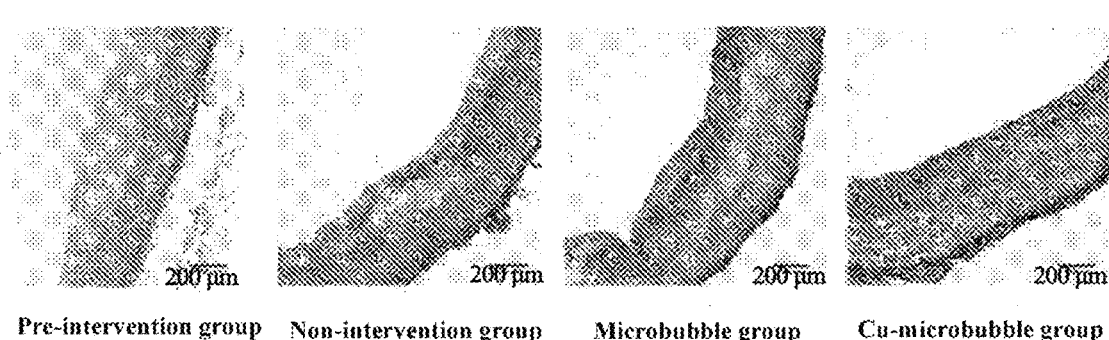
Figure 17:
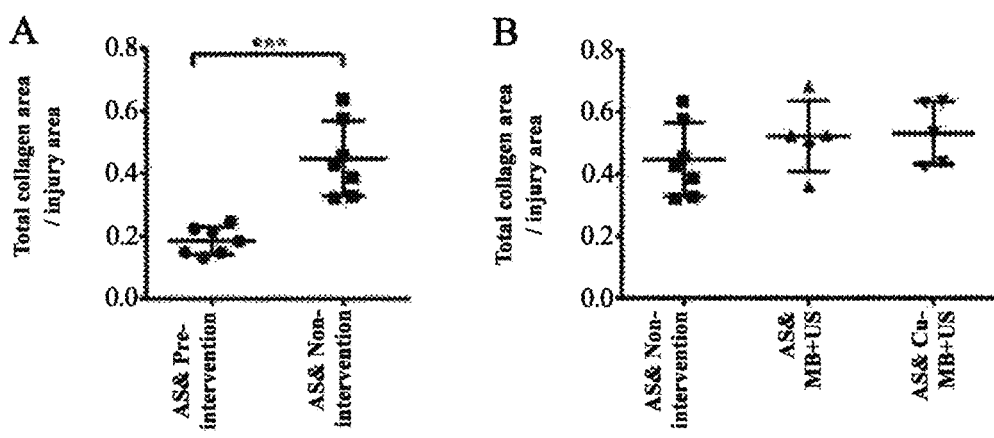
Figure 18:
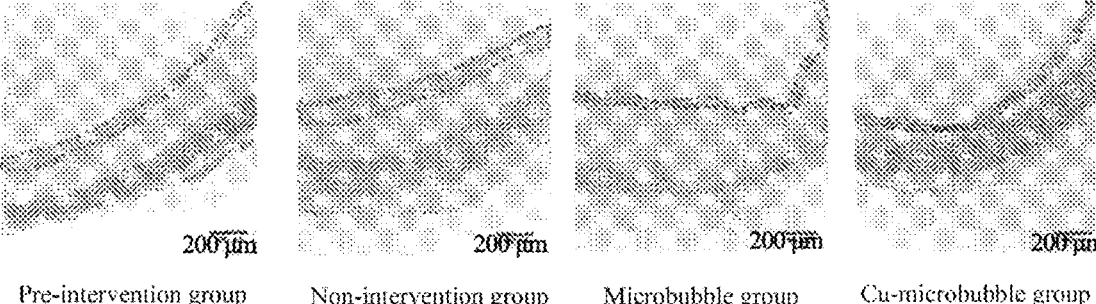
Figure 19:
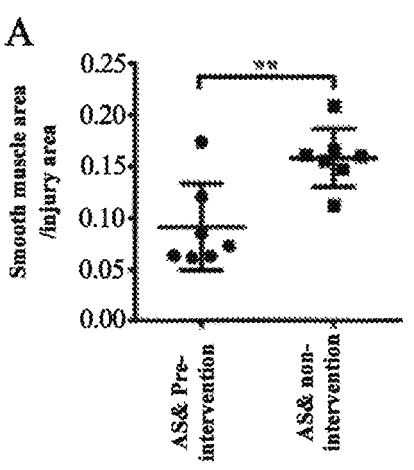
Figure 19:
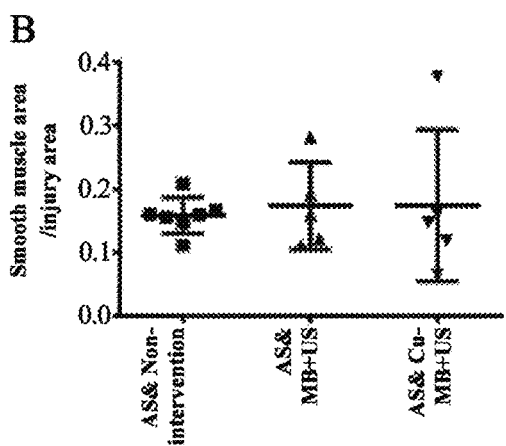
Figure 20:
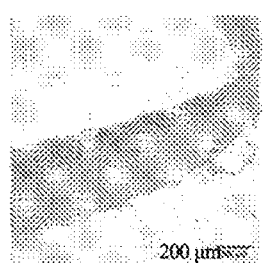
Figure 20:
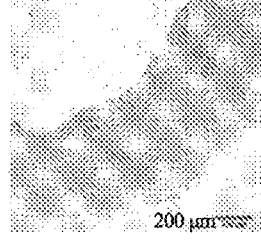
Figure 20:
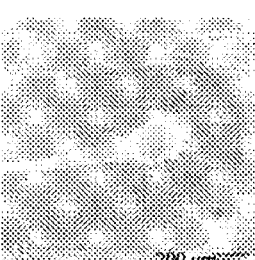
Figure 20:
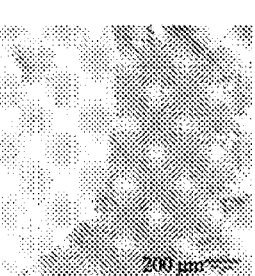
Figure 21:
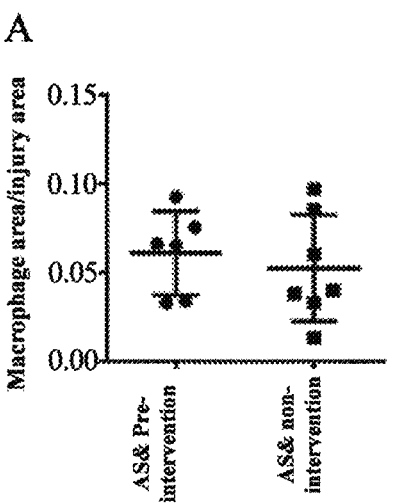
Figure 21:
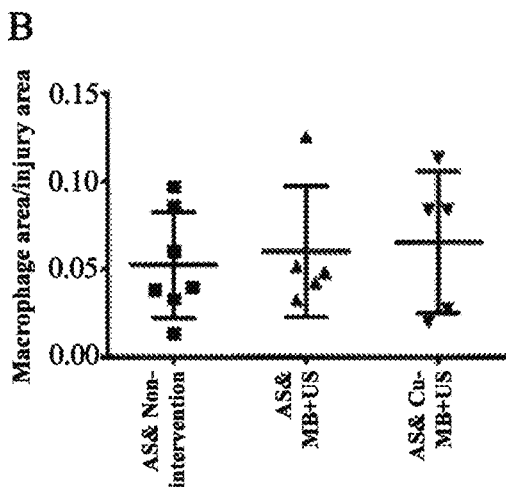
Figure 22:
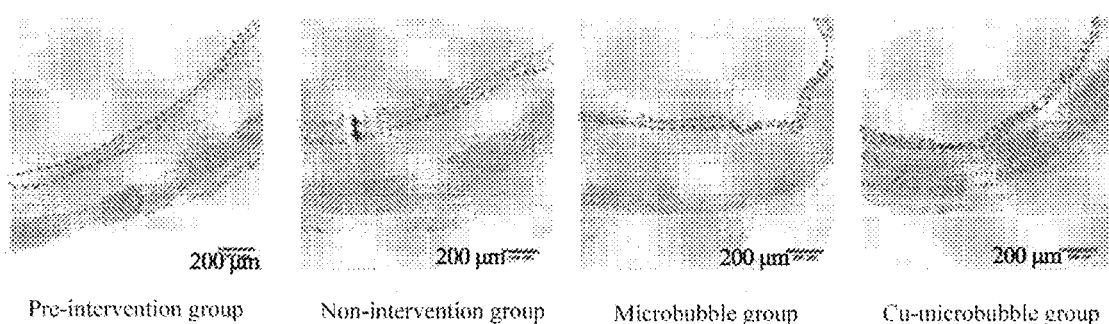
Figure 23:
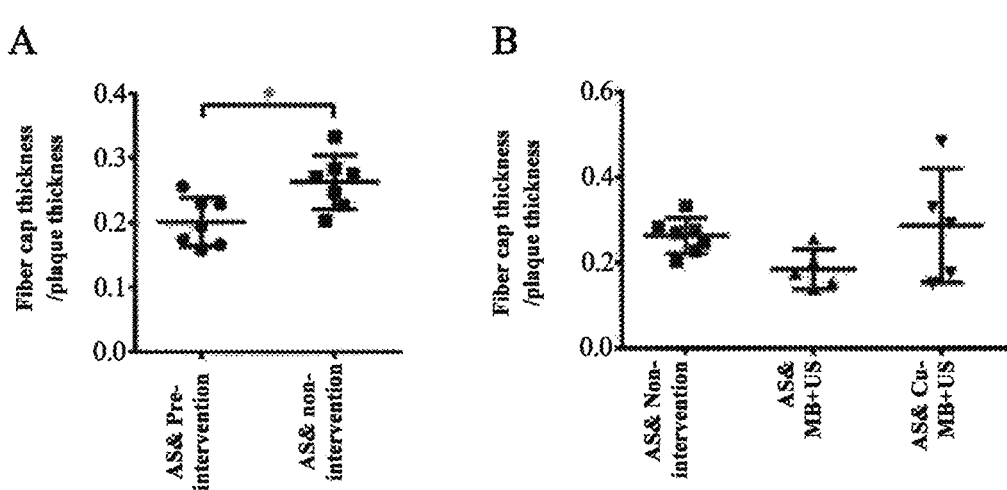
Figure 24:
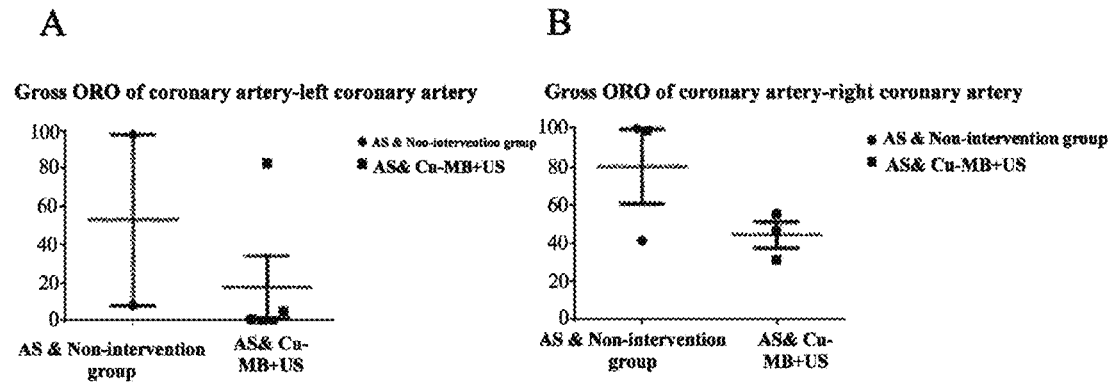
Figure 25:
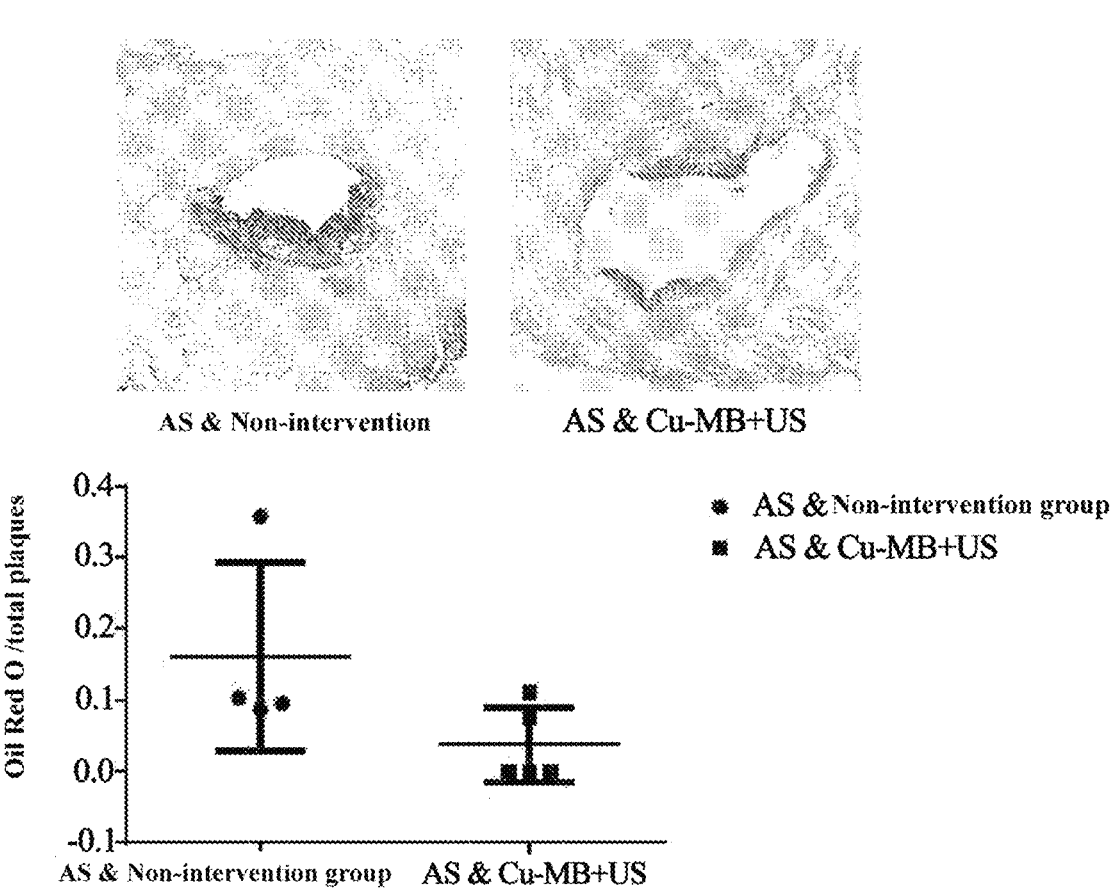
Figure 26:
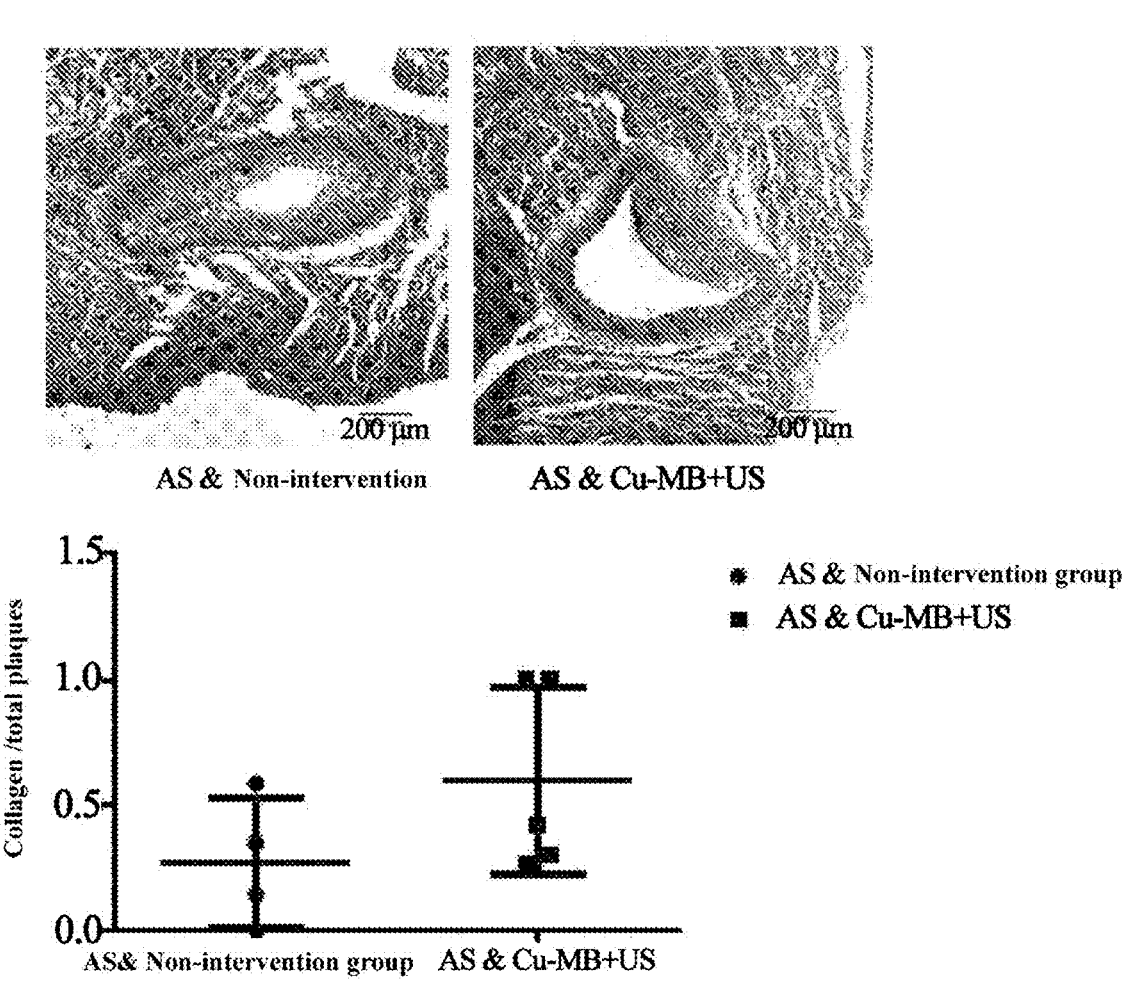
Figure 27:
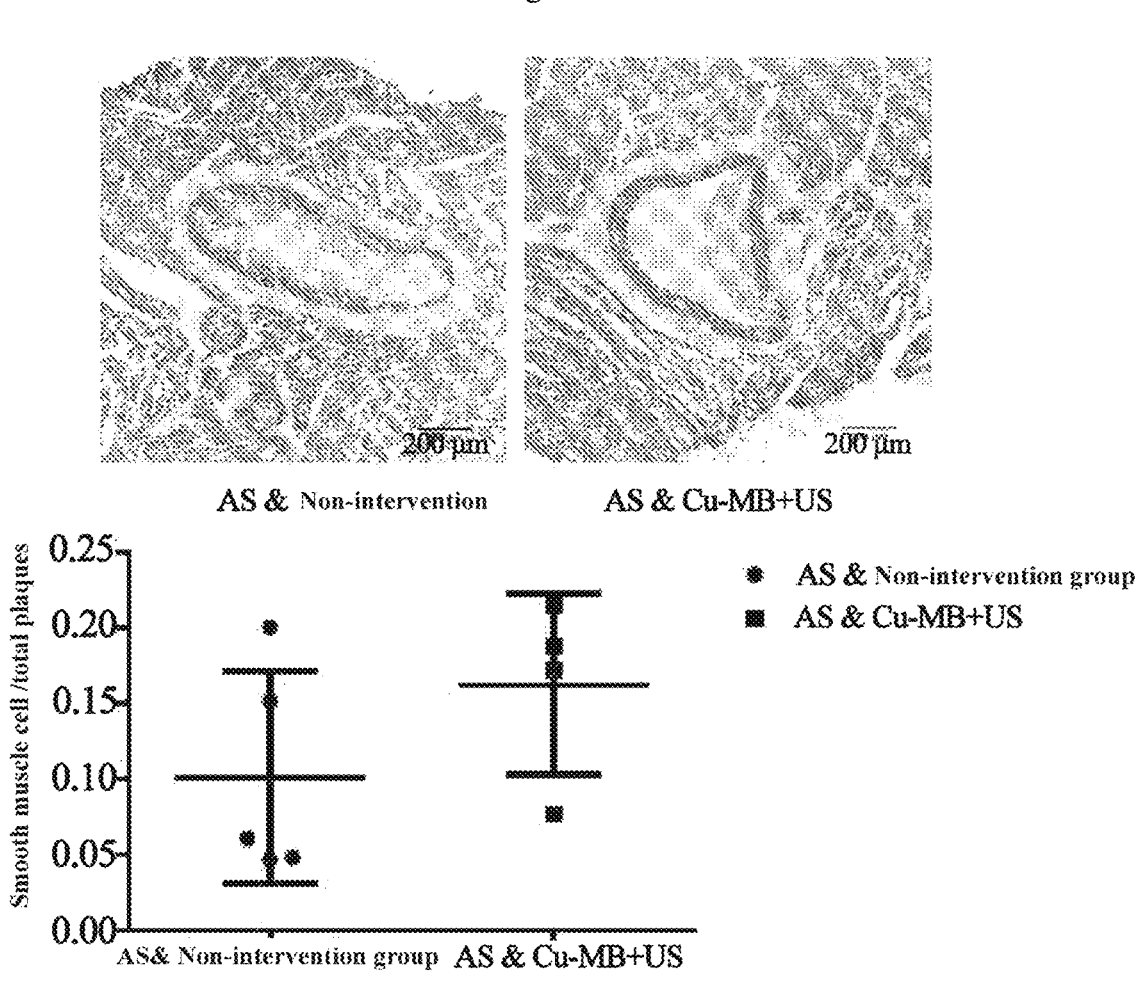
Figure 28:
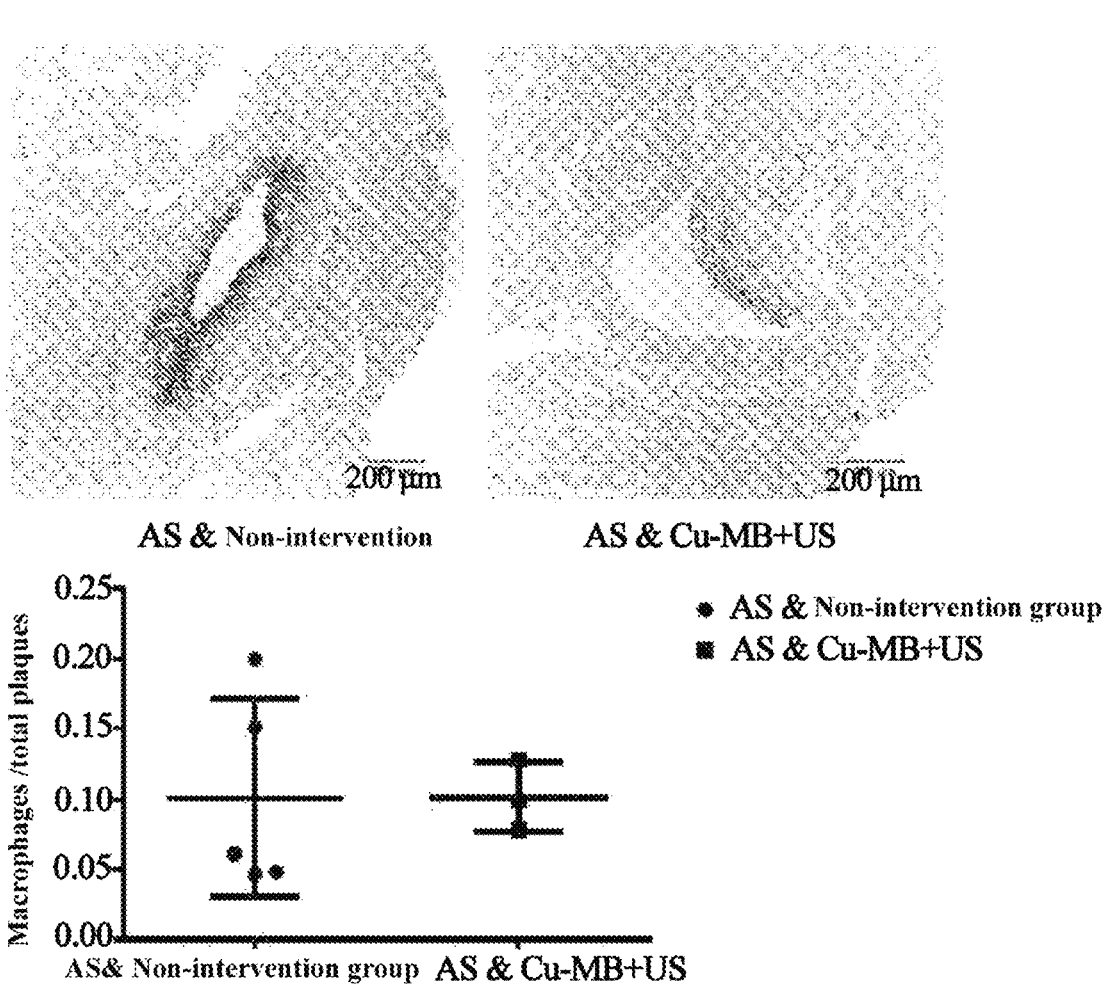

FIG. 6 is a light microscope photograph of the tissue sections stained with hematoxylin and eosin of different parts of the heart of the normal diet group and the high-cholesterol diet group after being fed for 12 weeks in the animal model experiment established in Example 3, wherein A is the left ventricular wall of the heart, B is the ventricular septum of the heart, and C is the right ventricular wall of the heart;

FIG. 7 shows the comparative results of copper content in the aortic intima-media of the normal diet group and the high-cholesterol diet group after being fed for 12 weeks in the animal model experiment established in Example 3, and two-sided test is performed for t-test, $*p<0.05$;

FIG. 8 shows the comparative results of copper contents in the heart (A), liver (B), spleen (C), and lung (D) in the normal diet group and the high-cholesterol diet group after being fed for 12 weeks in the animal model experiment established in Example 3, and two-sided test is performed for t-test, $*p<0.05$;

FIG. 9 is a diagram for comparing the detection results of serum total cholesterol (TC) content (A), low density lipoprotein cholesterol (LDL) content (B), high density lipoprotein cholesterol (HDL) content (C) and triglyceride (TG) content (D) in the normal diet group and the high-cholesterol diet group after being fed for 12 weeks in the animal model experiment established in Example 3, and two-sided test is performed for t-test, $*p<0.05$; $***0.0001<p<0.05$;

FIG. 10 is a statistical chart showing the percentage of plaque area relative to the vascular tiled area of the Oil Red O stained abdominal aorta after the intervention of each group of animals according to Example 4, wherein A is the statistical comparison of the plaque area percentage before intervention after modeling and the plaque area after three cycles of normal diet without intervention, it can be seen that under the condition of normal diet after modeling, the plaques continue to grow and increased by 94.73%; B is the statistical comparison of the plaque percentage after modeling between the intervened microbubble group and the Cu-microbubble group and the non-intervention group. Wherein compared with the microbubble group and the non-intervention group, the plaque area percentage in the Cu-microbubble group was significantly reduced, and two-sided test is performed for t-test, *p<0.05;

FIG. 11 is a microscope photograph of EVG stained sections of abdominal aorta elastic fiber of each group after the intervention of each group of animals according to Example 4;

FIG. 12 is a statistical chart of the plaque cross-sectional areas in the EVG stained sections of the abdominal aorta elastic fiber of each group after the intervention of each group of animals according to Example 4, A is the statistical comparison of the plaque area percentage in the pre-intervention group after modeling (AS & pre-intervention) with that of the plaque area after three cycles of normal diet (normal group) in the non-intervention group (AS & non-intervention). It can be seen that the plaque cross-sectional area increased by 37.39% under the condition of normal diet after modeling. B is the statistical comparison of the plaque percentages in the microbubble group (AS & MB+US) and the Cu-microbubble group (AS & Cu-MB+US) and the non-intervention group after three cycles of intervention after modeling, wherein compared with the microbubble group and the non-intervention group, the cross-sectional area of plaques in the Cu-microbubble group was significantly reduced by 45.75% and 27.16%, respectively;

FIG. 13 is a microscope photograph of sections stained with Oil Red O of abdominal aorta sections of each group after the intervention of each group of animals according to Example 4, wherein scale=200 μm;

FIG. 14 shows Staining for lipids in plaques using Oil Red O staining of frozen sections. Compared with the pre-intervention group (AS & pre-intervention), the lipid composition of abdominal aorta in the non-intervention group (AS & non-intervention) was unchanged. After three cycles of intervention, compared with the non-intervention group (AS & non-intervention), the lipid component in Cu-microbubble group (AS & Cu-MB+US) tended to decrease, with the reduction rate of 33.96%, and compared with the microbubble group (AS & MB+US), the reduction rate of the lipid component group was 53.15%; however, the lipid component in the microbubble group (AS & MB+US) tended to be increased compared with that in the non-intervention group (AS & Untreated);

FIG. 15 is a statistical analysis chart of the amounts of total cholesterol (TC), sphingomyelin (SM), free fatty acid (FFA), and triglycerides (TG) in the abdominal aorta of each group after the intervention of each group of animals according to Example 4;

FIG. 16 is a microscope photograph showing collagen components by Sirius Red-Fast Green FCF staining of sections after the intervention of each group of animals according to Example 4, wherein scale=200 μm;

FIG. 17 is a statistical analysis chart of the collagen component area in plaques after the sections are stained with Sirius Red-Fast Green FCF after the intervention of each group of animals according to Example 4;

FIG. 18 is a microscope photograph of each group in which smooth muscle cells are indicated by using α-SMA as a marker by using frozen section immunohistochemistry after the intervention of each group of animals according to Example 4, wherein scale=200 μm;

FIG. 19 is a statistical analysis chart of the ratio of the area of smooth muscle cells to the area of plaques indicated by using α-SMA as a marker by using frozen section immunohistochemistry after the intervention of each group of animals according to Example 4, wherein A is a statistical analysis chart of the ratio of the area of smooth muscle cells to the area of plaques comparing the pre-intervention (AS & pre-intervention) group and the non-intervention group (AS & non-intervention); B is a statistical analysis chart of the ratio of the area of smooth muscle cells to the area of plaques comparing the non-intervention group (AS & non-intervention), the microbubble group (AS & MB+US) and the Cu-microbubble group (AS & Cu-MB+US), and t-test, **0.001<P<0.05;

FIG. 20 is a microscope photograph of each group using CD68 as a marker by using paraffin section immunohistochemistry to indicate macrophages after the intervention of each group of animals according to Example 4, scale=200 μm;

FIG. 21 is a statistical analysis chart using CD68 as a marker by using paraffin section immunohistochemistry to indicate the ratio of the area of macrophages to the area of plaques after the intervention of each group of animals according to Example 4, wherein A is a statistical analysis chart comparing the ratios of the area of macrophages to the area of plaques of the pre-intervention group (AS & pre-intervention) and the non-intervention group (AS & non-intervention); B is a statistical analysis chart comparing the ratios of macrophage area to the area of plaques of the non-intervention group (AS & non-intervention), the microbubble group (AS & MB+US) and the Cu-microbubble group (AS & Cu-MB+US);

FIG. 22 is a microscope photograph of each group of smooth muscle cells indicated by using α-SMA as a marker by using frozen section immunohistochemistry after the intervention of each group of animals according to Example 4, and the thickness of the fibrous cap is indicated by the distribution on the side near the lumen of the plaque where the smooth muscle cells are located, in which as illustrated of the non-intervention group, the narrower part enclosed by the dotted line is the fibrous cap, the wider part enclosed by the dotted line is the plaque, and the scale=200 μm;

FIG. 23 is a statistical analysis chart of the ratio of the fibrous cap thickness to the plaque thickness indicated by using α-SMA as a marker by using frozen section immunohistochemistry after the intervention of each group of animals according to Example 4, wherein A is a statistical analysis chart comparing the ratio of the fibrous cap thickness to the plaque thickness of the pre-intervention group (AS & pre-intervention) and the non-intervention group (AS & non-intervention); B is a statistical analysis chart comparing the ratio of fibrous cap thickness to plaque thickness of the non-intervention group (AS & non-intervention), the microbubble group (AS & MB+US) and the Cu-microbubble group (AS & Cu-MB+US), and t-test, *p<0.05;

FIG. 24 is a statistical chart showing the percentage of plaque area relative to the percentage of the vascular tiled area after the coronary arteries are stained with Oil Red O after the intervention of each group of animals according to Example 5, wherein A is the material taken to observe from the left main coronary artery to the left anterior descending branch, the average plaque area of the blood vessel wall of the Cu-microbubble group is 17.86%, and the average plaque area on the blood vessel wall of the non-intervention group is 52.67%; B is a material taken to observe the right coronary artery, the average plaque area of the vascular wall of the intervention group is 43.87%, and the average plaque area of vascular wall of the non-intervention group is 79.92%;

FIG. 25 is a microscope photograph of an Oil Red O lipid stained section of the left coronary artery section and a diagram of calculating the area of the plaque occupied by lipid for statistical analysis after the intervention of each group of animals according to Example 5. Compared with the non-intervention group (AS & non-intervention), the lipid content of the Cu-microbubble group (AS & Cu-MB+ US) was reduced by 76.8%;

FIG. 26 is a microscope photograph of a Sirius Red-Fast Green FCF stained section of the left coronary artery section and a diagram of calculating the area of the plaque occupied by collagen for statistical analysis after the intervention of each group of animals according to Example 5. Compared with the non-intervention group (AS & non-intervention), the collagen content was doubled in the Cu-microbubble group (AS & Cu-MB+US);

FIG. 27 is a microscope photograph of a stained section of smooth muscle cells in the section of the left coronary artery and a diagram of calculating the area of the plaque occupied by smooth muscle cells for statistical analysis after the intervention of each group of animals according to Example 5. Compared with the non-intervention group (AS & non-intervention), the smooth muscle cell composition was increased by about 60% in the Cu-microbubble group (AS & Cu-MB+US);

FIG. 28 is a microscope photograph of a macrophage stained section in the left coronary artery section and a diagram of calculating the area of the plaque occupied by macrophages for statistical analysis after the intervention of each group of animals according to Example 5, there was no significant difference in macrophage composition between the Cu-microbubble group (AS & Cu-MB+US) and the non-intervention group (AS & non-intervention).

SPECIFIC MODES FOR CARRYING OUT THE EMBODIMENTS

The technical solutions in the embodiments of the present invention will be clearly and completely described below with reference to the embodiments of the present invention and the accompanying drawings, and obviously, the described embodiments are only a part of the embodiments of the present invention, but not all of the embodiments. Based on the embodiments in the present invention, all other embodiments obtained by a person of ordinary skill in the art without creative labor shall fall within the protection scope of the present invention.

Throughout the description, unless otherwise specified, the terms used herein are to be understood as having the meanings commonly used in the art. Therefore, unless otherwise defined, all technical and scientific terms used herein have the same meaning as commonly understood by one of ordinary skill in the art to which the present invention pertains. In case of contradiction, the present description takes precedence.

It should be noted that in the Examples of the present invention, the terms "comprise", "contain" or any other variations thereof are intended to cover non-exclusive inclusion, such that a method or apparatus that comprises a series of elements not only include those elements explicitly recited, but also other elements not explicitly recited, or inherent to the implementation of the method or apparatus. Without further limitation, an element defined by the phrase "comprising a . . . " does not preclude the presence of additional related elements in the method or apparatus that includes the element.

The composition of the present invention can be prepared by the following method.

For example, a fluid forming the core of the microbubbles can be filled into a dextrose solution containing a certain concentration of human serum albumin and a certain concentration of copper-containing ion source, and vibrated and mixed in an ultrasonic crusher to obtain a stable existing microbubble solution system. In this system, copper ions are stably combined with human serum albumin in the form of complexes. In which the copper ion source can be a water-soluble copper salt, such as copper sulfate, copper nitrate, copper chloride and the like.

The method of preparing the microbubbles of the present invention is not limited to the methods exemplified above. A more specific preparation method may be the method disclosed in Chinese Patent Application No. 201010223282.3, which is incorporated herein by reference in its entirety.

Example 1: Preparation and Stability Test of the Composition 5 wt % human serum albumin solution (HSA), copper sulfate solution ($CuSO_4$) of different concentrations as shown in Table 1 below and 5 wt % dextrose solution were mixed in a volume ratio of 3:1:9, and about 76.077 mL of perfluoropropane was filled into the mixed solution, and then the liquid-gas mixture was sonicated using an ultrasonic crusher (30% of the amplitude acts for 120 seconds, 80% of the amplitude acts for 30 seconds) to obtain a mixture of the present application, which is stored at 4° C.

The stability of the microbubble solution system was observed during storage at 4° C., wherein if microbubbles ruptured within 5 hours of standing, the microbubble solution system was considered extremely unstable (represented by X X); if microbubbles ruptured within 12 hours of standing, the microbubble solution system was considered unstable (represented by X); if microbubbles ruptured within 24 hours of standing, the microbubble solution system was considered stable (represented by Δ); if microbubbles did not rupture after standing for 1 to 3 months, the microbubble solution system was considered to be better in stability (represented by ○); and if microbubbles did not rupture after standing for 3 months or more, the microbubble solution system was considered to be excellent in stability (represented by ◎).

The colors of each obtained solutions were compared with the color plate, and the colors were qualitatively determined, and the storage stability was also observed. The results are shown in Table 1.

TABLE 1

| Color quality and stability of albumin-copper sulfate complex | | | | |
|---|---|---|---|---|
| No. | Concentration of the $CuSO_4$ solution | Color description | Color code | Stability |
| 1 | 0.5 mg/mL | Light fresh pink | FFCCCC | ○ |
| 2 | 0.8 mg/mL | Fresh pink | FF99CC | |
| 3 | 1.0 mg/mL | Periwinkle | FF99FF | ◎ |
| 4 | 1.2 mg/mL | Impatiens pink | FF66FF | ○ |
| 5 | 1.25 mg/mL | Lotus | FF66CC | ○ |
| 6 | 1.3 mg/mL | Dark pink | FF6699 | ○ |
| 7 | 1.35 mg/mL | Vivid pink | CC3366 | ○ |
| 8 | 1.4 mg/mL | Red lotus gray | CC6699 | Δ |
| 9 | 1.45 mg/mL | Cockscomb red | 993399 | Δ |
| 10 | 1.5 mg/mL | Green lotus | 993366 | X |
| 11 | 2.0 mg/mL | Dark reddish purple | 6633FF | X |
| 12 | 3.0 mg/mL | Cobalt blue | 3366CC | XX |

The results showed that the prepared copper-albumin microbubble solution system was pink and had good stability. Among them, the microbubble system prepared from 1.0 mg/mL $CuSO_4$ was the most stable and could be stably stored for more than 3 months in a refrigerator at 4° C. While the microbubble system prepared from 1.5 mg/mL, 2.0 mg/mL $CuSO_4$ solution was not stable enough, and the microbubbles ruptured after standing overnight; the copper-albumin microbubbles prepared from 3.0 mg/mL $CuSO_4$ solution had the worst stability, and the microbubbles ruptured after standing for 2 hours.

Figure 1:
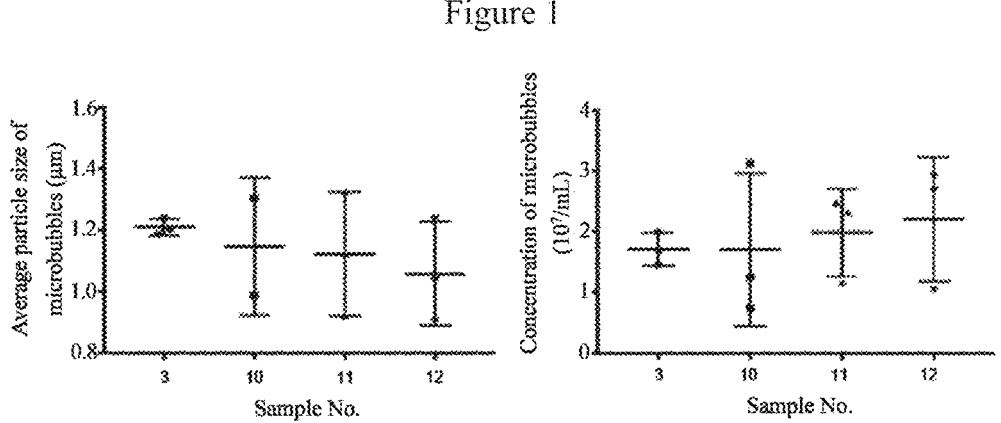
FIG. 1 shows the comparison of the differences in particle size and microbubble concentration measured for different

The particle size distribution and concentration of each batch of microbubbles were further detected, and it was found that the particle size distribution and concentration were uniform among all batches of the pink series microbubble system. The differences in particle size distribution and concentration between batches of other color systems are large. Referring to FIG. 1, the average particle size and concentration of No. 3 microbubble system are $1.21\pm0.03$ μm, and $(1.72\pm0.27)\times10^7$/mL, respectively; the average particle size and concentration of No. 10 microbubble system are $1.15\pm0.22$ and $(1.70\pm1.25)\times10^7$/mL, respectively; the average particle size and concentration of No. 11 microbubble system are $1.12\pm0.20$ and $(1.99\pm0.72)\times10^7$/mL, respectively; the average particle size and concentration of No. 12 microbubble system are $1.06\pm0.17$ μm, and $(2.21\pm1.02)\times10^7$/mL, respectively. Among them, the particle size distribution and concentration of copper albumin microbubbles prepared from 1.5 mg/mL, 2.0 mg/mL, and 3.0 mg/mL $CuSO_4$ solutions were significantly different.

It has been found by this stability example that a stable microbubble system can be obtained by mixing the albumin-containing solution and the copper ion-containing solution in an appropriate concentration and ratio, and the particle size of the microbubbles in the system fluctuates from batch to batch.

Example 2: Preparation of the Compositions of the Present Invention 5 wt % human albumin solution and 1 mg/mL copper sulfate solution were mixed in a ratio of 3:1, and then 76.077 mL of perfluoropropane was quantitatively filled into the albumin-copper sulfate mixed solution, and then the liquid-gas mixture was sonicated using an ultrasonic crusher (20 KHz) until the mixture becomes a pale pink emulsion suspension. Finally, it was detected that the average particle size of the microbubbles in the composition solution was about 1.05 μm, and the copper concentration was about $48.88\pm4.647$ μg/mL. The resulting solution was stored at 4° C. and used in the following examples.

5 wt % human serum albumin solution and 5 wt % dextrose solution were mixed in a ratio of 3:1, and then 38.04 mL of perfluoropropane was quantitatively filled into the 5% albumin-5% dextrose solution, and then the liquid-gas mixture was sonicated using an ultrasonic crusher (20 KHz) until the mixture becomes a white milky suspension. Finally, the average particle size of microbubbles and the average concentration of microbubbles in the composition solution were measured to be about 0.839 μm and $2.93\times10^7$/mL, respectively. The resulting solution was stored at 4° C. and used in the following examples.

Example 3: Establishment of Rabbit Atherosclerosis Model

In this experiment, high-cholesterol diet feeding method was adopted, and the high cholesterol feed was prepared by the Farm of Sichuan Experimental Animal Committee. The specific method is as follows: 1% by mass of cholesterol granules were added into the crushed common feed, mixed and then re-compressed into the granular feed containing high cholesterol. New Zealand white rabbits are sensitive to high cholesterol diets, and simply increasing the cholesterol in the diet can induce the formation of atherosclerotic lesions in animals, and the pathological process is similar to the pathological process of human in pathophysiology. Besides, diet induction without other intervention can better simulate human beings. Rabbit atherosclerosis model was established by feeding New Zealand white rabbits with the above-mentioned high cholesterol diet for 12 weeks.

Plaque formation in the aorta, cardiac lesions, copper loss in blood vessels and organs, and serum lipid content of normally fed animals and animals fed with high cholesterol diet were detected after modeling according to the sampling and determination method in Example 4 below.

Among them, Oil Red O staining of the abdominal aorta and thoracic aorta could clearly show that obvious red bulging plaques were visible under the intima of the abdominal aorta and thoracic aorta in rabbits fed with high cholesterol diet, while the intima of the thoracic aorta in rabbits fed with normal diet was smooth, and no plaque formation was seen (see FIG. 4). HE staining also showed that the intima bulged into the lumen on the transverse section of the abdominal aorta, and there were multinucleated vacuolar foam cells in the thickened intima (see FIG. 5). In addition, HE staining of tissues from different parts of the heart showed that blood vessels in various parts of the heart of rabbits in the high-cholesterol diet group had lesions, and adipose tissues were also found in the myocardium (see FIG. 6), and the vessels were nearly completely blocked due to severe lesions.

The aortic adventitia was peeled off, and the copper content of the aortic intima-media was determined by atomic absorption spectrometry, it was found that the copper content in the aorta of the high-cholesterol diet group was significantly decreased (by about 39%) as compared with that of the normal diet group (see FIG. 7), and in other organs (such as heart (A), liver (B), spleen (C), and lung (D)), the copper content was also significantly decreased (see FIG. 8).

In addition, referring to FIG. 9, the contents of total cholesterol (TC, A in FIG. 9), low density lipoprotein cholesterol (LDL, B in FIG. 9), high density lipoprotein cholesterol (HDL, C in FIG. 9) and triglycerides (TG, D in FIG. 9) in serum were measured and compared, and it was found that the amounts of total cholesterol and low density lipoprotein cholesterol in serum of the high cholesterol diet group were significantly higher than those of the normal diet group, and the average content of triglycerides in serum was also 2.25 times than that of the normal diet group.

Thus proving the success of modeling.

Example 4: Effect of the Composition of the Present Invention on Atherosclerotic Plaque Grouping and Processing Method:

After one week of adaptive feeding, 44 New Zealand white rabbits were randomly assigned into a normal diet group (n=11) and an atherosclerotic lesion group (n=33) according to body weight. Rabbit atherosclerosis model was established by feeding with high cholesterol diet for 12 weeks. After modeling, the rabbits were randomly assigned into four groups according to body weight, in which one group being the pre-intervention group (AS & pre-intervention, n=7), and meanwhile, 5 rabbits in the normal diet group were randomly selected according to body weight to be compared with the pre-intervention group (normal-1 group). The materials were collected from the two groups immediately after modeling. The remaining three groups were non-intervention groups (AS & non-intervention, n=8), Cu-microbubble group (AS & Cu-MB+US, n=9), and microbubble group (AS & MB+US, n=9). The remaining normal diet groups were designated as normal groups (n=6). Detailed process and grouping are shown in FIG. 2.

Intervention Method:

The rabbits were fixed on the fixation plate in the supine position and the abdominal coat was removed. During the intervention, 5 mL of reagent was injected in five times, with a rapid bolus of 1 mL each time, and at the same time, ultrasound with a mechanical index of 1.2 (Philips iU22 probe L9-3) was used to target rupture at the abdominal aorta about 5 cm away from the celiac trunk for release, the release time per milliliter of reagent is 1 minute. The intervention was terminated after the complete release of the reagent was observed by ultrasound imaging. The AS & MB+US group and the AS & Cu-MB+US group were intervened once every three days, with 8 interventions as a cycle, a total of three cycles (24 times in total). AS & non-intervention group only repeated the operation of immobilizing rabbits without any liquid injection.

Sampling and Determination Method:

After the animals were weighed and blood collected at the end of the experiment, the materials were collected.

Blood collection: Fasting blood was collected from middle auricular arteries of rabbits.

Aorta: Animals were anesthetized to death by an overdose of sodium pentobarbital (1.5 mL/kg dose) via the auricular vein. The rabbit was cut along the midline of the rabbit's abdomen to expose the abdomen, and then the aorta was peeled off. The four branches of the celiac trunk, the superior mesenteric artery, the right renal artery and the left renal artery were ligated in turn to mark the location and prevent major bleeding. After thoracotomy, the entire aorta was further taken out, and the blood vessels were rinsed in normal saline until pale yellow. The thoracic and abdominal aorta are bounded by the diaphragm.

Tissue allocation of the aorta: the blood vessel was cut into three sections with a blade (FIG. 3): the first section of blood vessel 1 was used for pathological sectioning for histological examination; in the second section of blood vessel, the left half blood vessel 2 was used for gross ORO staining, the right blood vessel 3 was used for copper detection; and the third blood vessel 4 is stored in liquid nitrogen for lipid composition detection and analysis.

Serum Biochemical Analysis: blood samples were analyzed for total cholesterol (TC), low-density lipoprotein cholesterol (LDL), high-density lipoprotein cholesterol (HDL) and triglycerides (TG) by colorimetry.

Oil Red O staining of fresh tissue (gross ORO staining): after the tissue was fixed in paraformaldehyde for 10 minutes, it was stained with ORO. After staining, the aortic intima was peeled off, with the plaque-containing intima facing upward, and the Stereoscopic observation was performed, pictures were collected, and Photoshop software was used to measure the intimal area and plaque area.

Oil Red O staining of frozen sections: the frozen sections were stained with ORO staining solution and counterstained with hematoxylin Immediately after mounting, the plaques were observed and photographed under a microscope. Image Pro-Plus 6.0 software was used to measure the plaque area and ORO positive area, and the ratio of the positive area to the total plaque area was calculated.

Sirius Red-Fast Green FCF staining: the paraffin sections were stained with Sirius Red-Fast Green FCF staining solution. After mounting, 100× microscope was used to observe and take pictures. Image Pro-Plus 6.0 software was used to measure the plaque area and Sirius Red positive area, and the ratio of the positive area to the total plaque area was calculated.

Elastic fiber staining: the paraffin sections were dyed black with Verhoff's working solution, and color separation was conducted with 2% ferric chloride color separation solution to make the elastic fibers black and other components gray. Finally, the resultants were counterstained in VG staining solution to make the background light red Images were collected under a microscope immediately after mounting.

Immunohistochemical processing immunohistochemical processing was performed according to the conventional method, and the sections after sealing could be stored at room temperature. The images were observed and taken under a 100-fold microscope. Image Pro-Plus 6.0 software was used to outline the morphology of the plaques, and statistical analysis on the size of the positive expression areas in the plaques was performed.

Detection of copper concentration: the concentrations of copper in serum and tissues were determined by atomic absorption spectrometry (Atomic Absorption Spectroscopy, ICE3500, Thermo Corporation).

Detection of lipid content in abdominal aorta: the contents of total cholesterol (TC), sphingomyelin (SM), free fatty acid (FFA) and triglyceride (TG) in abdominal aorta were detected by colorimetry.

Plaque vulnerability index: studies suggest that macrophages and lipids in plaques are components that promote the instability of plaques, while smooth muscle cells and collagen are components that promote cell stability. Therefore, the vulnerability index of plaques was calculated according to the following formula:

Plaque vulnerability index=(macrophages %+lipid components %)/(smooth muscle cells %+collagen %).

Data processing and statistical analysis: all experimental data in this study were analyzed using SPSS 20.0 statistical analysis software. Student t test was used for univariate analysis of the two groups, and One-way ANOVA was used to compare the non-intervention group (AS & non-intervention), the microbubble group (AS & MB+US) and the Cu-microbubble group (AS & Cu-MB+US). When the differences of three groups in One-way ANOVA comparison were statistically significant, further comparison between two groups shall be conducted by SNK. When the data did not conform to the normal distribution, the rank sum test was used, with $\alpha=0.05$ as the test level, and $p<0.05$ was considered statistically significant.

Test Results:

4.1. Changes in Atherosclerotic Plaque Size 4.1.1 Changes in Percentage of Atherosclerotic Plaque Area After modeling, intervention was performed according to the aforementioned intervention method, and the percentage of plaque area relative to vascular tiled area was calculated according to the results of Oil Red O staining. The results are shown in Table 2 below. In addition, the statistical results of plaque areas in each group of abdominal aorta part are shown in FIG. 10.

TABLE 2

| Plaque location | | AS & pre-intervention | AS & non-intervention | AS & MB + US | AS & Cu-MB + US |
|---|---|---|---|---|---|
| Plaque area | Abdominal aorta | 41.57% | 80.96% | 87.58% | 51.63% |
| | Thoracic aorta | 68.42% | 83.29% | 89.59% | 57.75% |

As shown in Table 2 and FIG. 10, under the action of copper, the area percentage of atherosclerotic plaques was significantly reduced, with significant differences as compared with the non-intervention group and the group without copper in the microbubbles (p<0.05).

4.1.2 Cross-Sectional Area of Atheroma

The elastic fiber EVG-stained section of the abdominal aortic cross-section was further observed (see FIG. 11, wherein the plaque cross-section was within the dashed line) and the plaque area in the vascular cross-section was calculated for statistical analysis as shown in FIG. 12.

As shown in FIGS. 11 and 12, compared with the pre-intervention group (AS & pre-intervention), the cross-sectional area of plaques in the abdominal aorta section of the non-intervention group (AS & non-intervention) continued to grow, with a growth rate of 37.39% (A in FIG. 12). The plaque cross-sectional area of AS & MB+US group was even larger than that of the gross of the non-intervention group; while the Cu-microbubble group (AS & Cu-MB+US) showed a significant reduction, with the plaque area reduced by 27.16% compared with the non-intervention group and 45.75% compared with the microbubble group.

The above results indicated that Cu ion played a vital role in inhibiting the growth of plaques and reducing the size of plaques. Only the cavitation of the microbubbles themselves at the lesion site has little inhibition on the growth of plaques.

4.2. Plaque Stability Changes 4.2.1. Change in Lipid Composition in Plaques

The Oil Red O lipid-stained sections of the abdominal aorta were observed (see FIG. 13), and the lipid fraction in the plaque area was calculated for statistical analysis (see FIG. 14).

As shown in FIG. 13, the lipids in the plaques were significantly reduced in the Cu-microbubble group (AS & Cu-MB+US) compared with those in the microbubble group (AS & MB+US) and the non-intervention group (AS & non-intervention). Among them, compared with the microbubble group, the lipid component in the Cu-microbubble group was reduced by 33.96%; and compared with the non-intervention group, the lipid component was reduced by 53.15%.

The amounts of total cholesterol (TC), sphingomyelin (SM), free fatty acid (FFA) and triglyceride (TG) in abdominal aorta of each group were further detected and statistically analyzed, as shown in FIG. 15. Among them, compared with the untreated group, in the Cu-microbubble group, the total cholesterol was reduced by 52.1%, the sphingomyelin was reduced by 57%, and the free fatty acid was reduced by 40.5%; and compared with the microbubble group, the total cholesterol was reduced by 49.7%, the sphingomyelin was reduced by 42.3%, and the free fatty acid was reduced by 55.5%.

4.2.2. Changes in Collagen Composition in Plaques

The sections of each group stained with Sirius Red-Fast Green FCF were observed, in which red indicates the collagen component (see FIG. 16), and a statistical analysis of the area of the collagen component is shown in FIG. 17.

Among them, compared with the pre-intervention group (AS & pre-intervention), the collagen content in the non-intervention group (AS & non-intervention) was significantly increased, the collagen contents in the microbubble group (AS & MB+US) and Cu-microbubble group (AS & Cu-MB+US) were further increased, and the Cu-microbubble group showed an increasing trend compared with the microbubble group, with a growth rate of 17.14%.

It is generally believed that the more collagen component in plaques, the better for the stability of plaques. From the results of the respective experiments mentioned above, it could be seen that the collagen components in the microbubble group and the Cu-microbubble group were slightly increased.

4.2.3. Changes in the Proportion of Smooth Muscle Cells in Plaques

The smooth muscle cells were indicated by using α-SMA as a marker by using frozen section immunohistochemistry. The ratio of the area of smooth muscle cells in the plaque to the area of the plaque (the portion surrounded by the dotted line in FIG. 18) was calculated and shown in FIG. 19. Among them, compared with the pre-intervention group (AS & pre-intervention), the smooth muscle cell content in plaques increased by nearly 40% in the non-intervention group (AS & non-intervention) (A in FIG. 19), while there was no significant difference among the non-intervention group, the microbubble group (AS & MB+US) and the Cu-microbubble group (AS & Cu-MB+US) (B in FIG. 19).

It is generally believed that the more smooth muscle in the plaque, the better the stability of the plaque. It can be seen from the results of the respective experiments described above that the composition of the present invention has no effect on smooth muscle.

4.2.4. Changes in the Proportion of Macrophages in Plaques

Using paraffin section immunohistochemistry, CD68 was used as a marker to indicate the macrophages (see FIG. 20), and the unstable factors were reflected by the ratios of macrophage area to plaque area. The statistical analysis chart was shown in FIG. 21. It can be seen from FIG. 21 that there was no significant difference in the ratio of macrophage area to plaque area between the groups.

It is generally believed that the fewer macrophages in the plaque, the better the stability of the plaque. As can be seen from the results of the respective experiments described above, the composition of the present invention has no significant effect on the number of macrophages.

4.2.5. Variation of Fibrous Cap Thickness in Plaques

The smooth muscle cells were indicated by using α-SMA as a marker by using frozen section immunohistochemistry. The thickness of the fibrous cap was indicated by the distribution on the side near the lumen of the plaque where the smooth muscle cells were located. The ratio of the thickness of the fibrous cap in the plaque (the narrower part enclosed by the dotted line in FIG. 22) to the thickness of the plaque (the wider part enclosed by the dotted line in FIG. 22) is calculated and is shown in FIG. 23. Among them, compared with the pre-intervention group (AS & pre-intervention), the ratio of fibrous cap to plaque thickness was significantly increased in the non-intervention group (AS & non-intervention) (A in FIG. 23), while there was no significant change among the non-intervention group, the microbubble group (AS & MB+US) and the Cu-microbubble group (AS & Cu-MB+US) (B in FIG. 23).

In general, the change in the thickness of the fibrous cap is an indicator of the change in plaque structure. The larger the ratio of the fibrous cap thickness to the plaque thickness, the more stable the plaque. It can be seen from FIG. 22 that the thickness of the fibrous cap and the thickness of the plaque in the Cu-microbubble group were both decreased compared with the non-intervention group, but the ratio did not change significantly. The statistical results indicate that the composition of the present invention does not significantly affect the ratio of the fibrous cap to the plaque thickness.

4.2.6. Changes in Plaque Vulnerability Index

The vulnerability index of the plaque was calculated basing on the parameters measured in 4.2.1 to 4.2.4 above. The vulnerability index of plaques is calculated according to the following formula:

$$Plaque\ vulnerability\ index=(macrophages\ \%+lipid\ components\ \%)/(smooth\ muscle\ cells\ \%+collagen\ \%).$$

In the above formula, macrophages %, lipid components %, smooth muscle cell % and collagen % are the percentages of the areas of macrophages, lipid components, smooth muscle cells and collagen measured above in the plaque area, respectively. The calculated average plaque vulnerability index of each group is shown in Table 3 below.

TABLE 3

| Group | Pre-intervention group | Non-intervention group | Microbubble group | Cu-microbubble group |
|---|---|---|---|---|
| Plaque vulnerability index | 0.415 | 0.239 | 0.264 | 0.196 |

Example 5: Effect of the Composition of the Present Invention on Coronary Atherosclerotic Plaque Establishment of rabbit atherosclerosis model in this Example is the same as that in Example 3, and the microbubble composition used was prepared in Example 2.

8 New Zealand white rabbits were treated in a similar manner as in Example 4, and divided into a non-intervention group (AS & non-intervention) (n=3) and a Cu-microbubble group (AS & Cu-MB+US)(n=5).

Sampling Method is as Follows:

Coronary Artery Sampling:

Sampling of left coronary artery: the left main coronary artery and left anterior descending branch were separated from the aortic root to the apex, and the total length of sampling was about 1.3 cm, in which the left coronary artery of 0.3 cm near the aortic root was used for pathological sectioning, and the remaining about 1 cm was used for gross ORO analysis.

Right coronary artery sampling: the right coronary artery was separated from the aortic root to the right ventricle, and the total length of the sampling was about 1.3 cm, in which the right coronary artery of 0.3 cm close to the aortic root was used for pathological sectioning, and the remaining about 1 cm was used for gross ORO analysis.

Test Results:

5.1 Changes in Atherosclerotic Plaque Size 5.1.1 Change in Percentage of Atherosclerotic Plaque Area After modeling, intervention was performed according to the aforementioned intervention method, and the percentage of plaque area relative to vascular tiled area was calculated according to the results of Oil Red O staining. The results are shown in Table 4 below. In addition, the statistical results of plaque areas in each group of left and right coronary arteries are shown in FIG. 24.

TABLE 4

| Plaque position | AS & non-intervention | AS & Cu-MB + US |
|---|---|---|
| Left coronary artery | 52.69% | 17.86% |
| Right coronary artery | 79.92% | 43.87% |

5.2 Plaque Stability Changes 5.2.1. Changes in Lipid Composition in Plaques

The Oil Red O lipid-stained sections of the abdominal aorta were observed (see FIG. 25), and the lipid fraction in the plaque area was calculated for statistical analysis (see FIG. 25). Compared with the non-intervention group, the lipid composition of the Cu-microbubble group (AS&Cu-MB+US) was reduced by 76.8%.

5.2.2 Changes in Collagen Composition in Plaques

The sections stained with Sirius Red-Fast Green FCF were observed in the left coronary vein (see FIG. 26), and the area of collagen accounted for plaques was calculated for statistical analysis (see FIG. 26). The collagen composition of the Cu-microbubble group (AS&Cu-MB+US) was doubled compared to the non-intervention group.

It is generally believed that the more collagen component in plaques, the better for the stability of plaques. From the results of the respective experiments mentioned above, it could be seen that the collagen components in the Cu-microbubble group was doubled compared with that in the non-intervention group.

5.2.3 Changes in the Proportion of Smooth Muscle Cells in Plaques

The stained sections of smooth muscle cells in the cross section of the left coronary artery were observed (see FIG. 27), and the area of smooth muscle cells in the plaque was calculated for statistical analysis (see FIG. 27). The smooth muscle cell composition was increased by approximately 60% in the Cu-microbubble group (AS & Cu-MB+US) compared with the non-intervention group.

It is generally believed that the more smooth muscle in the plaque, the better the stability of the plaque. It can be seen from the results of the respective experiments described above that the smooth muscle cell composition was increased by approximately 60% in the Cu-microbubble group (AS & Cu-MB+US) compared with the non-intervention group.

5.2.4 Changes in the Proportion of Macrophages in Plaques

The stained sections of macrophages in the cross section of the left coronary artery were observed (see FIG. 28), and the area occupied by macrophages in plaques was calculated for statistical analysis (see FIG. 28). There was no significant difference in the macrophage composition between the Cu-microbubble group (AS & Cu-MB+US) and the non-intervention group.

It is generally believed that the fewer macrophages in the plaque, the better the stability of the plaque. As can be seen from the results of the respective experiments described above, the composition of the present invention has no significant effect on the number of macrophages.

It can be seen that the intervention of the composition of the present invention combined with ultrasonic treatment does not affect the stability of the plaque and has a trend of enhancing the stability of the plaque, while the simple microbubbles combined with ultrasonic treatment has a trend of reducing the stability of the plaque. This result suggested that, unlike the previous proposal of using microbubble cavitation to break up plaques, the effect of Cu ions on plaques may be to reduce plaques in situ and prevent plaques from shedding to some extent.

The above description are only preferred embodiments of the present invention, and are not intended to limit the patent scope of the present invention. Under the inventive concept of the present invention, the equivalent structure transformation made by the contents of the description and drawings of the present invention, or directly/indirectly applied to other relevant technical fields are all included in the scope of patent protection of the present invention.

What is claimed is:

1. A method for treatment of atherosclerosis, comprising:

injecting a composition into a blood vessel of a subject in need of the treatment, and applying external energy to a vascular site to be treated, wherein the composition comprises a solution comprising microbubbles having a concentration greater than $1\times10^6$ number of microbubbles per mL and a particle size less than 10 μm and an effective therapeutic amount of copper ions, wherein the microbubble has a core-envelope structure, the core of the microbubble contains a fluid, and the envelope of the microbubble is composed of a pharmaceutically acceptable film-forming material, wherein the fluid contained in the core of the microbubble has a boiling point under standard conditions of lower than 35° C., and is one selected from the group consisting of air, carbon dioxide and C1-6 fluoroalkanes, wherein the microbubbles have an average diameter of 1 to 5 μm, wherein the effective therapeutic amount of $Cu^{2+}$ is $Cu^{2+}$ is a concentration of 35 to 105 mg/mL in the composition.

2. The method according to claim 1, wherein the fluid contained in the core of the microbubble has a boiling point under standard conditions of lower than 30° C., and is perfluoropropane.

3. The method according to claim 1, wherein the pharmaceutically acceptable film-forming material is albumin or a phospholipid material.

4. The method according to claim 1, wherein the copper ion and the pharmaceutically acceptable film-forming material form a complex.

5. The method according to claim 1, wherein the surface of the envelope of the microbubble further has a targeting moiety, wherein the targeting moiety is a chemical group having a substituent that can chelate calcium, the substituent is at least one selected from an amino group, a carboxyl group, a phosphoryl group, and a sulfydryl group.

6. The method according to claim 1, wherein the concentration of the microbubbles is $0.5\times10^7$ to $1.5\times10^7$ number of microbubbles per mL.

7. The method according to claim 1, wherein the microbubbles have an average diameter of 1 to 2 μm.

8. The method according to claim 1, wherein the effective therapeutic amount of $Cu^{2+}$ is $Cu^{2+}$ having a concentration of 45 to 85 mg/mL in the composition.

9. The method according to claim 1, wherein the composition further comprises a pharmaceutically acceptable carrier.

10. The method according to claim 1, wherein the microbubbles are cavitated under the action of external energy.

11. The method according to claim 1, wherein the treatment of atherosclerosis is inhibiting atherosclerotic plaque size growth and/or reducing atherosclerotic plaque size.

12. The method according to claim 3, wherein the pharmaceutically acceptable film-forming material is human serum albumin.

13. The method according to claim 4, wherein the copper ion and the pharmaceutically acceptable film-forming material form a chelate.

14. The method according to claim 5, wherein the targeting moiety has a bisphosphonate group.

15. The method according to claim 6, wherein the concentration of the microbubbles is $1.0\times10^7$ to $1.3\times10^7$ number of microbubbles per mL.

16. The method according to claim 9, wherein the carrier may be a dextrose solution, physiological saline or deionized water.

17. The method according to claim 10, wherein the energy is ultrasonic energy or electromagnetic energy.

* * * * *